(12) United States Patent
Guo et al.

(10) Patent No.: US 12,129,520 B2
(45) Date of Patent: Oct. 29, 2024

(54) DNA SEQUENCING METHOD

(71) Applicant: PEKING UNIVERSITY, Beijing (CN)

(72) Inventors: Xuefeng Guo, Beijing (CN); Xiaolong Wang, Beijing (CN); Haina Ci, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 746 days.

(21) Appl. No.: 16/327,535

(22) PCT Filed: Oct. 30, 2017

(86) PCT No.: PCT/CN2017/108325
§ 371 (c)(1),
(2) Date: Feb. 22, 2019

(87) PCT Pub. No.: WO2018/041274
PCT Pub. Date: Mar. 8, 2018

(65) Prior Publication Data
US 2019/0330695 A1  Oct. 31, 2019

(30) Foreign Application Priority Data

Aug. 31, 2016 (CN) .......................... 201610798113.X

(51) Int. Cl.
*C12M 1/34* (2006.01)
*C12N 9/12* (2006.01)
(Continued)

(52) U.S. Cl.
CPC ......... *C12Q 1/6876* (2013.01); *C12N 9/1252* (2013.01); *H10K 85/40* (2023.02);
(Continued)

(58) Field of Classification Search
USPC ............. 435/6.1, 6.11, 6.12, 7.1, 91.1, 91.2; 436/94, 501; 536/300, 350
See application file for complete search history.

(56) References Cited

U.S. PATENT DOCUMENTS

| 6,451,191 B1 * | 9/2002 | Bentsen ........... G01N 27/44791 204/600 |
| 2014/0174927 A1 * | 6/2014 | Bashir .................. C12Q 1/6827 204/452 |

(Continued)

FOREIGN PATENT DOCUMENTS

| CN | 102643893 A | 8/2012 |
| CN | 104359946 A | 2/2015 |

(Continued)

OTHER PUBLICATIONS

First Office Action of Japanese Patent Application No. 2019-506126 dated Apr. 10, 2020; 7 pgs.

(Continued)

*Primary Examiner* — Frank W Lu
(74) *Attorney, Agent, or Firm* — Umberg Zipser LLP

(57) ABSTRACT

Disclosed is a DNA sequencing method. The DNA sequencing method of this invention comprises: (1) adding a tag sequence at the 3' terminus of the DNA to be sequenced so as to form a DNA to be sequenced including the tag sequence, the nucleotide sequence of said tag sequence being the reverse complement of the nucleotide sequence of the sequencing primer; (2) mixing the DNA to be sequenced including the tag sequence and the sequencing primer so as to form a product having a 5' terminus double strand and a single main strand; (3) after step (2) is completed, the product is mixed separately with dATP, dCTP, dTTP, and dGTP to obtain four systems, each system is separately added to a single-molecule device modified by a DNA polymerase, and electric signals are read. Experiments verify that the method of this invention performs DNA sequencing and has important application value.

6 Claims, 12 Drawing Sheets

Specification includes a Sequence Listing.

(51) Int. Cl.
*C12Q 1/6876* (2018.01)
*H10K 85/40* (2023.01)
*B82Y 15/00* (2011.01)
*B82Y 30/00* (2011.01)
*B82Y 35/00* (2011.01)

(52) U.S. Cl.
CPC .............. *B82Y 15/00* (2013.01); *B82Y 30/00* (2013.01); *B82Y 35/00* (2013.01); *C12Y 207/07007* (2013.01)

(56) References Cited

U.S. PATENT DOCUMENTS

| | | | |
|---|---|---|---|
| 2014/0235462 A1* | 8/2014 | Kotseroglou | .... C12Q 2521/101 506/3 |
| 2016/0017416 A1 | 1/2016 | Boyanov et al. | |
| 2017/0138925 A1* | 5/2017 | Kim | .................. B81C 1/00087 |

FOREIGN PATENT DOCUMENTS

| | | |
|---|---|---|
| CN | 104630358 A | 5/2015 |
| CN | 105092647 A | 11/2015 |
| CN | 106244712 A | 12/2016 |
| JP | 2017521082 A | 8/2017 |
| WO | 2010068884 A2 | 6/2010 |
| WO | 2012005857 A1 | 1/2012 |
| WO | 2014182630 A1 | 11/2014 |
| WO | 2016100635 A1 | 6/2016 |

OTHER PUBLICATIONS

WP_000250009_1, DNA polymerase I [*Escherichia coli*], Feb. 23, 2019.

Extended European Search Report dated Sep. 27, 2019 for European Application No. 17845576.2; 7 pages.

Chen et al., "DNA sequencing using electrical conductance measurements of a DNA polymerase," Nature Nanotechnology, May 5, 2013; 8:452-458.

First Office Action of Chinese Application No. 201610798113X issued by the CNIPA on Mar. 12, 2019; 10 pgs.

International Search Report dated Mar. 8, 2018 for Application No. PCT/CN2017/108325; 6 pgs.

\* cited by examiner (II)

(1) (2)

(3) (4)

E

A

B

C

E

E

E

SEQUENCE LISTING

```
<160> NUMBER OF SEQ ID NOS: 14

<210> SEQ ID NO 1
<211> LENGTH: 928
<212> TYPE: PRT
<213> ORGANISM: Escherichia coli

<400> SEQUENCE: 1

Met Val Gln Ile Pro Gln Asn Pro Leu Ile Leu Val Asp Gly Ser Ser
1               5                   10                  15

Tyr Leu Tyr Arg Ala Tyr His Ala Phe Pro Pro Leu Thr Asn Ser Ala
            20                  25                  30

Gly Glu Pro Thr Gly Ala Met Tyr Gly Val Leu Asn Met Leu Arg Ser
        35                  40                  45

Leu Ile Met Gln Tyr Lys Pro Thr His Ala Ala Val Val Phe Asp Ala
    50                  55                  60

Lys Gly Lys Thr Phe Arg Asp Glu Leu Phe Glu His Tyr Lys Ser His
65                  70                  75                  80

Arg Pro Pro Met Pro Asp Asp Leu Arg Ala Gln Ile Glu Pro Leu His
                85                  90                  95

Ala Met Val Lys Ala Met Gly Leu Pro Leu Leu Ala Val Ser Gly Val
            100                 105                 110

Glu Ala Asp Asp Val Ile Gly Thr Leu Ala Arg Glu Ala Glu Lys Ala
        115                 120                 125

Gly Arg Pro Val Leu Ile Ser Thr Gly Asp Lys Asp Met Ala Gln Leu
    130                 135                 140

Val Thr Pro Asn Ile Thr Leu Ile Asn Thr Met Thr Asn Thr Ile Leu
145                 150                 155                 160

Gly Pro Glu Glu Val Val Asn Lys Tyr Gly Val Pro Pro Glu Leu Ile
                165                 170                 175
```

```
Ile Asp Phe Leu Ala Leu Met Gly Asp Ser Ser Asp Asn Ile Pro Gly
            180                 185                 190

Val Pro Gly Val Gly Glu Lys Thr Ala Gln Ala Leu Leu Gln Gly Leu
            195                 200                 205

Gly Gly Leu Asp Thr Leu Tyr Ala Glu Pro Glu Lys Ile Ala Gly Leu
            210                 215                 220

Ser Phe Arg Gly Ala Lys Thr Met Ala Ala Lys Leu Glu Gln Asn Lys
225                 230                 235                 240

Glu Val Ala Tyr Leu Ser Tyr Gln Leu Ala Thr Ile Lys Thr Asp Val
                245                 250                 255

Glu Leu Glu Leu Thr Cys Glu Gln Leu Glu Val Gln Gln Pro Ala Ala
            260                 265                 270

Glu Glu Leu Leu Gly Leu Phe Lys Lys Tyr Glu Phe Lys Arg Trp Thr
            275                 280                 285

Ala Asp Val Glu Ala Gly Lys Trp Leu Gln Ala Lys Gly Ala Lys Pro
            290                 295                 300

Ala Ala Lys Pro Gln Glu Thr Ser Val Ala Asp Glu Ala Pro Glu Val
305                 310                 315                 320

Thr Ala Thr Val Ile Ser Tyr Asp Asn Tyr Val Thr Ile Leu Asp Glu
                325                 330                 335

Glu Thr Leu Lys Ala Trp Ile Ala Lys Leu Glu Lys Ala Pro Val Phe
            340                 345                 350

Ala Phe Asp Thr Glu Thr Asp Ser Leu Asp Asn Ile Ser Ala Asn Leu
            355                 360                 365

Val Gly Leu Ser Phe Ala Ile Glu Pro Gly Val Ala Ala Tyr Ile Pro
            370                 375                 380

Val Ala His Asp Tyr Leu Asp Ala Pro Asp Gln Ile Ser Arg Glu Arg
385                 390                 395                 400

Ala Leu Glu Leu Leu Lys Pro Leu Leu Glu Asp Glu Lys Ala Leu Lys
                405                 410                 415

Val Gly Gln Asn Leu Lys Tyr Asp Arg Gly Ile Leu Ala Asn Tyr Gly
            420                 425                 430

Ile Glu Leu Arg Gly Ile Ala Phe Asp Thr Met Leu Glu Ser Tyr Ile
            435                 440                 445

Leu Asn Ser Val Ala Gly Arg His Asp Met Asp Ser Leu Ala Glu Arg
            450                 455                 460

Trp Leu Lys His Lys Thr Ile Thr Phe Glu Glu Ile Ala Gly Lys Gly
465                 470                 475                 480

Lys Asn Gln Leu Thr Phe Asn Gln Ile Ala Leu Glu Glu Ala Gly Arg
                485                 490                 495

Tyr Ala Ala Glu Asp Ala Asp Val Thr Leu Gln Leu His Leu Lys Met
            500                 505                 510

Trp Pro Asp Leu Gln Lys His Lys Gly Pro Leu Asn Val Phe Glu Asn
            515                 520                 525

Ile Glu Met Pro Leu Val Pro Val Leu Ser Arg Ile Glu Arg Asn Gly
            530                 535                 540

Val Lys Ile Asp Pro Lys Val Leu His Asn His Ser Glu Glu Leu Thr
545                 550                 555                 560

Leu Arg Leu Ala Glu Leu Glu Lys Lys Ala His Glu Ile Ala Gly Glu
                565                 570                 575

Glu Phe Asn Leu Ser Ser Thr Lys Gln Leu Gln Thr Ile Leu Phe Glu
            580                 585                 590
```

```
Lys Gln Gly Ile Lys Pro Leu Lys Thr Pro Gly Ala Pro Ser
            595                 600                 605
Thr Ser Glu Glu Val Leu Glu Glu Leu Ala Leu Asp Tyr Pro Leu Pro
    610                 615                 620
Lys Val Ile Leu Glu Tyr Arg Gly Leu Ala Lys Leu Lys Ser Thr Tyr
625                 630                 635                 640
Thr Asp Lys Leu Pro Leu Met Ile Asn Pro Lys Thr Gly Arg Val His
                645                 650                 655
Thr Ser Tyr His Gln Ala Val Thr Ala Thr Gly Arg Leu Ser Ser Thr
            660                 665                 670
Asp Pro Asn Leu Gln Asn Ile Pro Val Arg Asn Glu Glu Gly Arg Arg
        675                 680                 685
Ile Arg Gln Ala Phe Ile Ala Pro Glu Asp Tyr Val Ile Val Ser Ala
690                 695                 700
Asp Tyr Ser Gln Ile Glu Leu Arg Ile Met Ala His Leu Ser Arg Asp
705                 710                 715                 720
Lys Gly Leu Leu Thr Ala Phe Ala Glu Gly Lys Asp Ile His Arg Ala
                725                 730                 735
Thr Ala Ala Glu Val Phe Gly Leu Pro Leu Glu Thr Val Thr Ser Glu
            740                 745                 750
Gln Arg Arg Ser Ala Lys Ala Ile Asn Phe Gly Leu Ile Tyr Gly Met
        755                 760                 765
Ser Ala Phe Gly Leu Ala Arg Gln Leu Asn Ile Pro Arg Lys Glu Ala
770                 775                 780
Gln Lys Tyr Met Asp Leu Tyr Phe Glu Arg Tyr Pro Gly Val Leu Gln
785                 790                 795                 800
Tyr Met Glu Arg Thr Arg Ala Gln Ala Lys Glu Gln Gly Tyr Val Glu
                805                 810                 815
Thr Leu Asp Gly Arg Arg Leu Tyr Leu Pro Asp Ile Lys Ser Ser Asn
            820                 825                 830
Gly Ala Arg Arg Ala Ala Ala Glu Arg Ala Ala Ile Asn Ala Pro Met
        835                 840                 845
Gln Gly Thr Ala Ala Asp Ile Ile Lys Arg Ala Met Ile Ala Val Asp
850                 855                 860
Ala Trp Leu Gln Ala Glu Gln Pro Arg Val Arg Met Ile Met Gln Val
865                 870                 875                 880
His Asp Glu Leu Val Phe Glu Val His Lys Asp Asp Val Asp Ala Val
                885                 890                 895
Ala Lys Gln Ile His Gln Leu Met Glu Asn Cys Thr Arg Leu Asp Val
            900                 905                 910
Pro Leu Leu Val Glu Val Gly Ser Gly Glu Asn Trp Asp Gln Ala His
        915                 920                 925

<210> SEQ ID NO 2
<211> LENGTH: 2787
<212> TYPE: DNA
<213> ORGANISM: Escherichia coli

<400> SEQUENCE: 2
atggttcaga tcccccaaaa tccacttatc cttgtagatg gttcatctta tctttatcgc      60
gcatatcacg cgtttccccc gctgactaac agcgcaggcg agccgaccgg tgcgatgtat     120
ggtgtcctca acatgctgcg cagtctgatc atgcaatata aaccgacgca tgcagcggtg     180
gtctttgacg ccaagggaaa aaccttcgt gatgaactgt ttgaacatta caaatcacat     240
```

```
cgcccgccaa tgccggacga tctgcgtgca caaatcgaac ccttgcacgc gatggttaaa    300
gcgatgggac tgccgctgct ggcggtttct ggcgtagaag cggacgacgt tatcggtact    360
ctggcgcgcg aagccgaaaa agccgggcgt ccggtgctga tcagcactgg cgataaagat    420
atggcgcagc tggtgacgcc aaatattacg cttatcaaca ctatgacgaa taccatcctc    480
ggaccggaag aggtggtgaa taagtacggc gtgccgccag aattgatcat cgacttcctg    540
gcgctgatgg gtgactcctc tgataacatt ccaggcgtac cgggcgtcgg tgaaaaaacc    600
gcgcaggcat tgctgcaagg tcttggcggc ctggatacgc tgtatgccga gccagaaaaa    660
attgctgggt tgagcttccg tggcgcgaaa acaatggcag cgaagctcga gcaaaacaaa    720
gaagttgctt atctctcata ccagctggcg acgattaaaa ccgacgttga actggagctg    780
acctgtgaac aactgaagt gcagcaaccg gcagcggaag agttgttggg gctgttcaaa    840
aagtatgagt tcaaacgctg gactgctgat gtcgaagcgg gcaaatggtt acaggccaaa    900
ggggcaaaac cagccgcgaa gccacaggaa accagtgttg cagacgaagc accagaagtg    960
acggcaacgg tgatttctta tgacaactac gtcaccatcc ttgatgaaga aacactgaaa   1020
gcgtggattg cgaagctgga aaaagcgccg gtatttgcat ttgataccga aaccgacagc   1080
cttgataaca tctctgctaa cctggtcggg cttttcttttg ctatcgagcc aggcgtagcg   1140
gcatatattc cggttgctca tgattatctt gatgcgcccg atcaaatctc tcgcgagcgt   1200
gcactcgagt tgctaaaacc gctgctggaa gatgaaaagg cgctgaaggt cgggcaaaac   1260
ctgaaatacg atcgcggtat tctggcgaat tacggcattg agctgcgtgg gattgcgttt   1320
gataccatgc tggagtccta cattctcaat agcgttgccg ggcgtcacga tatggacagc   1380
ctcgcggaac gttggttgaa gcacaaaacc atcactttg aagagattgc gggtaaaggc   1440
aaaaatcaac tgacctttaa ccagattgcc ctcgaagagg ccggacgtta cgccgccgaa   1500
gatgcagatg tcaccttgca gctgcatctg aaaatgtggc cggatctgca aaaacacaaa   1560
gggccgttga cgtcttcga gaatatcgaa atgccgctag tgccggtgct ttcacgcatt   1620
gaacgtaacg gtgtgaagat cgatccgaaa gtgctgcaca atcattctga agagctcact   1680
cttcgtctgg ctgagctgga aaagaaagcg catgaaattg caggtgagga gtttaacctt   1740
tcttccacca agcagttaca aaccattctg tttgaaaaac agggcattaa accgctgaag   1800
aaaacgccag gtggcgcgcc gtcaacgtcg aagaggtac tggaagaact ggcgctggac   1860
tatccgttgc caaaagtgat tctggagtat cgtggtctgg cgaagctgaa atcgacttac   1920
accgacaagc tgccgctgat gatcaacccg aaaaccgggc gtgtgcatac ctcttatcac   1980
caggcagtaa ctgcaacggg acgtttatcg tcaaccgatc ctaacctgca aaacattccg   2040
gtgcgtaacg aagaaggtcg tcgtatccgc caggcgttta ttgcgccaga ggattatgtg   2100
attgtctcgg cggactactc gcagattgaa ctgcgcatta tggcgcatct ctcgcgtgac   2160
aaaggcttgc tgaccgcatt cgcggaagga aagatatcc accgggctac ggcggcagaa   2220
gtgtttggtt tgccactgga aaccgtaacc agcgagcaac gccgtagcgc gaaagcgatc   2280
aactttggtc tgatttatgg catgagtgct ttcggtctgg cgcggcaatt gaacattcca   2340
cgtaaagaag cgcagaagta catgaccctt tacttcgaac gctacctgg cgtgctgcag   2400 tatatggaac gcacccgtgc tcaggcgaaa gagcagggct acgttgaaac gctggacgga   2460
cgccgtctgt atctgccgga tatcaaatcc agcaatgggg ctcgtcgtgc agcggctgaa   2520
cgtgcagcca ttaacgcgcc aatgcaggga accgccgccg acattatcaa acgggcgatg   2580
attgccgttg atgcgtggct acaggctgag caaccgcgtg tacgtatgat catgcaggta   2640
```

-continued

```
cacgatgaac tggtatttga agttcataaa gatgatgtcg atgccgtcgc gaagcagatt    2700
catcaactga tggaaaactg tacccgtctg gatgtgccgc tgctggtgga agtggggagt    2760
ggcgaaaact gggatcaggc gcactaa                                        2787
```

<210> SEQ ID NO 3
<211> LENGTH: 928
<212> TYPE: PRT
<213> ORGANISM: Artificial Sequence
<220> FEATURE:
<223> OTHER INFORMATION: Reconstructed DNA pol I

<400> SEQUENCE: 3

```
Met Val Gln Ile Pro Gln Asn Pro Leu Ile Leu Val Asp Gly Ser Ser
1               5                   10                  15

Tyr Leu Tyr Arg Ala Tyr His Ala Phe Pro Pro Leu Thr Asn Ser Ala
            20                  25                  30

Gly Glu Pro Thr Gly Ala Met Tyr Gly Val Leu Asn Met Leu Arg Ser
        35                  40                  45

Leu Ile Met Gln Tyr Lys Pro Thr His Ala Ala Val Val Phe Asp Ala
    50                  55                  60

Lys Gly Lys Thr Phe Arg Asp Glu Leu Phe Glu His Tyr Lys Ser His
65                  70                  75                  80

Arg Pro Pro Met Pro Asp Asp Leu Arg Ala Gln Ile Glu Pro Leu His
                85                  90                  95

Ala Met Val Lys Ala Met Gly Leu Pro Leu Leu Ala Val Ser Gly Val
            100                 105                 110

Glu Ala Asp Asp Val Ile Gly Thr Leu Ala Arg Glu Ala Glu Lys Ala
        115                 120                 125

Gly Arg Pro Val Leu Ile Ser Thr Gly Asp Lys Asp Met Ala Gln Leu
    130                 135                 140

Val Thr Pro Asn Ile Thr Leu Ile Asn Thr Met Thr Asn Thr Ile Leu
145                 150                 155                 160

Gly Pro Glu Glu Val Val Asn Lys Tyr Gly Val Pro Pro Glu Leu Ile
                165                 170                 175

Ile Asp Phe Leu Ala Leu Met Gly Asp Ser Ser Asp Asn Ile Pro Gly
            180                 185                 190

Val Pro Gly Val Gly Glu Lys Thr Ala Gln Ala Leu Leu Gln Gly Leu
        195                 200                 205

Gly Gly Leu Asp Thr Leu Tyr Ala Glu Pro Glu Lys Ile Ala Gly Leu
    210                 215                 220

Ser Phe Arg Gly Ala Lys Thr Met Ala Ala Lys Leu Glu Gln Asn Lys
225                 230                 235                 240

Glu Val Ala Tyr Leu Ser Tyr Gln Leu Ala Thr Ile Lys Thr Asp Val
                245                 250                 255

Glu Leu Glu Leu Thr Cys Glu Gln Leu Glu Val Gln Gln Pro Ala Ala
            260                 265                 270

Glu Glu Leu Leu Gly Leu Phe Lys Lys Tyr Glu Phe Lys Arg Trp Thr
        275                 280                 285

Ala Asp Val Glu Ala Gly Lys Trp Leu Gln Ala Lys Gly Ala Lys Pro
    290                 295                 300

Ala Ala Lys Pro Gln Glu Thr Ser Val Ala Asp Glu Ala Pro Glu Val
305                 310                 315                 320

Thr Ala Thr Val Ile Ser Tyr Asp Asn Tyr Val Thr Ile Leu Asp Glu
                325                 330                 335
```

```
Glu Thr Leu Lys Ala Trp Ile Ala Lys Leu Glu Lys Ala Pro Val Phe
            340                 345                 350

Ala Phe Asp Thr Glu Thr Asp Ser Leu Asp Asn Ile Ser Ala Asn Leu
            355                 360                 365

Val Gly Leu Ser Phe Ala Ile Glu Pro Gly Val Ala Ala Tyr Ile Pro
            370                 375                 380

Val Ala His Asp Tyr Leu Asp Ala Pro Asp Gln Ile Ser Arg Glu Arg
385                 390                 395                 400

Ala Leu Glu Leu Leu Lys Pro Leu Leu Glu Asp Lys Ala Leu Lys
            405                 410                 415

Val Gly Gln Asn Leu Lys Tyr Asp Arg Gly Ile Leu Ala Asn Tyr Gly
            420                 425                 430

Ile Glu Leu Arg Gly Ile Ala Phe Asp Thr Met Leu Glu Ser Tyr Ile
            435                 440                 445

Leu Asn Ser Val Ala Gly Arg His Asp Met Asp Ser Leu Ala Glu Arg
            450                 455                 460

Trp Leu Lys His Lys Thr Ile Thr Phe Glu Glu Ile Ala Gly Lys Gly
465                 470                 475                 480

Lys Asn Gln Leu Thr Phe Asn Gln Ile Ala Leu Glu Glu Ala Gly Arg
            485                 490                 495

Tyr Ala Ala Glu Asp Ala Asp Val Thr Leu Gln Leu His Leu Lys Met
            500                 505                 510

Trp Pro Asp Leu Gln Lys His Lys Gly Pro Leu Asn Val Phe Glu Asn
            515                 520                 525

Ile Glu Met Pro Leu Val Pro Val Leu Ser Arg Ile Glu Arg Asn Gly
            530                 535                 540

Val Lys Ile Asp Pro Lys Val Leu His Asn His Ser Glu Glu Leu Thr
545                 550                 555                 560

Leu Arg Leu Ala Glu Leu Glu Lys Lys Ala His Glu Ile Ala Gly Glu
            565                 570                 575

Glu Phe Asn Leu Ser Ser Thr Lys Gln Leu Gln Thr Ile Leu Phe Glu
            580                 585                 590

Lys Gln Gly Ile Lys Pro Leu Lys Lys Thr Pro Gly Gly Ala Pro Ser
            595                 600                 605

Thr Ser Glu Glu Val Leu Glu Glu Leu Ala Leu Asp Tyr Pro Leu Pro
            610                 615                 620

Lys Val Ile Leu Glu Tyr Arg Gly Leu Ala Lys Leu Lys Ser Thr Tyr
625                 630                 635                 640

Thr Asp Lys Leu Pro Leu Met Ile Asn Pro Lys Thr Gly Arg Val His
            645                 650                 655

Thr Ser Tyr His Gln Ala Val Thr Ala Thr Gly Arg Leu Ser Ser Thr
            660                 665                 670

Asp Pro Asn Leu Gln Asn Ile Pro Val Arg Asn Glu Glu Gly Arg Arg
            675                 680                 685

Ile Arg Gln Ala Phe Ile Ala Pro Glu Asp Tyr Val Ile Val Ser Ala
            690                 695                 700

Asp Tyr Ser Gln Ile Glu Leu Arg Ile Met Ala His Leu Ser Arg Asp
705                 710                 715                 720

Lys Gly Leu Leu Thr Ala Phe Ala Glu Gly Lys Asp Ile His Arg Ala
            725                 730                 735

Thr Ala Ala Glu Val Phe Gly Leu Pro Leu Glu Thr Val Thr Ser Glu
            740                 745                 750
```

```
Gln Arg Arg Ser Ala Lys Ala Ile Asn Phe Gly Leu Ile Tyr Gly Met
            755                 760                 765

Ser Ala Phe Gly Leu Ala Arg Gln Leu Asn Ile Pro Arg Lys Glu Ala
    770                 775                 780

Gln Lys Tyr Met Asp Cys Tyr Phe Glu Arg Tyr Pro Gly Val Leu Gln
785                 790                 795                 800

Tyr Met Glu Arg Thr Arg Ala Gln Ala Lys Glu Gln Gly Tyr Val Glu
                805                 810                 815

Thr Leu Asp Gly Arg Arg Leu Tyr Leu Pro Asp Ile Lys Ser Ser Asn
            820                 825                 830

Gly Ala Arg Arg Ala Ala Ala Glu Arg Ala Ala Ile Asn Ala Pro Met
        835                 840                 845

Gln Gly Thr Ala Ala Asp Ile Ile Lys Arg Ala Met Ile Ala Val Asp
850                 855                 860

Ala Trp Leu Gln Ala Glu Gln Pro Arg Val Arg Met Ile Met Gln Val
865                 870                 875                 880

His Asp Glu Leu Val Phe Glu Val His Lys Asp Val Asp Ala Val
                885                 890                 895

Ala Lys Gln Ile His Gln Leu Met Glu Asn Ser Thr Arg Leu Asp Val
            900                 905                 910

Pro Leu Leu Val Glu Val Gly Ser Gly Glu Asn Trp Asp Gln Ala His
        915                 920                 925

<210> SEQ ID NO 4
<211> LENGTH: 68
<212> TYPE: DNA
<213> ORGANISM: Artificial Sequence
<220> FEATURE:
<223> OTHER INFORMATION: Synthetic sequence for DNA I

<400> SEQUENCE: 4
cccccccccc cccccccccc cccccccccc cccccccccc cccccccccc actggccgtc     60
gttttaca                                                              68

<210> SEQ ID NO 5
<211> LENGTH: 18
<212> TYPE: DNA
<213> ORGANISM: artificial sequence
<220> FEATURE:
<223> OTHER INFORMATION: Synthetic sequence for DNA II

<400> SEQUENCE: 5
tgtaaaacga cggccagt                                                   18

<210> SEQ ID NO 6
<211> LENGTH: 68
<212> TYPE: DNA
<213> ORGANISM: Artificial Sequence
<220> FEATURE:
<223> OTHER INFORMATION: Synthetic sequence for DNA III

<400> SEQUENCE: 6
aaaaaaaaaa aaaaaaaaaa aaaaaaaaaa aaaaaaaaaa aaaaaaaaaa actggccgtc     60
gttttaca                                                              68

<210> SEQ ID NO 7
<211> LENGTH: 68
<212> TYPE: DNA
<213> ORGANISM: Artificial Sequence
<220> FEATURE:
```

<223> OTHER INFORMATION: Synthetic sequence for DNA IV

<400> SEQUENCE: 7

```
gggggggggg gggggggggg gggggggggg gggggggggg gggggggggg actggccgtc    60
gttttaca                                                             68
```

<210> SEQ ID NO 8
<211> LENGTH: 68
<212> TYPE: DNA
<213> ORGANISM: Artificial Sequence
<220> FEATURE:
<223> OTHER INFORMATION: Synthetic Sequence for DNA V

<400> SEQUENCE: 8

```
tttttttttt tttttttttt tttttttttt tttttttttt tttttttttt actggccgtc    60
gttttaca                                                             68
```

<210> SEQ ID NO 9
<211> LENGTH: 64
<212> TYPE: DNA
<213> ORGANISM: Artificial Sequence
<220> FEATURE:
<223> OTHER INFORMATION: Synthetic Sequence for DNA VI

<400> SEQUENCE: 9

```
tgctagctgc taattgtctc catgtcatgt agctagctgt cacagtactg gccgtcgttt    60
taca                                                                 64
```

<210> SEQ ID NO 10
<211> LENGTH: 50
<212> TYPE: DNA
<213> ORGANISM: Artificial Sequence
<220> FEATURE:
<223> OTHER INFORMATION: Synthetic sequence

<400> SEQUENCE: 10

```
cccccccccc cccccccccc cccccccccc cccccccccc cccccccccc                50
```

<210> SEQ ID NO 11
<211> LENGTH: 50
<212> TYPE: DNA
<213> ORGANISM: Artificial Sequence
<220> FEATURE:
<223> OTHER INFORMATION: Synthetic sequence

<400> SEQUENCE: 11

```
aaaaaaaaaa aaaaaaaaaa aaaaaaaaaa aaaaaaaaaa aaaaaaaaaa                50
```

<210> SEQ ID NO 12
<211> LENGTH: 50
<212> TYPE: DNA
<213> ORGANISM: Artificial Sequence
<220> FEATURE:
<223> OTHER INFORMATION: Synthetic sequence

<400> SEQUENCE: 12

```
gggggggggg gggggggggg gggggggggg gggggggggg gggggggggg                50
```

<210> SEQ ID NO 13
<211> LENGTH: 50
<212> TYPE: DNA
<213> ORGANISM: Artificial Sequence
<220> FEATURE:
<223> OTHER INFORMATION: Synthetic sequence

```
<400> SEQUENCE: 13
tttttttttt tttttttttt tttttttttt tttttttttt tttttttttt            50

<210> SEQ ID NO 14
<211> LENGTH: 46
<212> TYPE: DNA
<213> ORGANISM: Artificial Sequence
<220> FEATURE:
<223> OTHER INFORMATION: Synthetic sequence

<400> SEQUENCE: 14
tgctagctgc taattgtctc catgtcatgt agctagctgt cacagt                46
```

DNA SEQUENCING METHOD

This application claims priority of Chinese Patent Application No. 201610798113.X, filed with the State Intellectual Property Office on Aug. 31, 2016, entitled "DNA sequencing method", which are incorporated herein by reference in its entirety.

INCORPORATION BY REFERENCE

The instant application contains a Sequence Listing which has been submitted in ASCII format via EFS-Web and is hereby incorporated by reference in its entirety. Said ASCII copy was amended on Jul. 25, 2019, is named 104140-002US1AMIDSEQLIST2.txt, and is 22,475 bytes in size.

FIELD OF THE INVENTION

The present invention relates to the field of biotechnology, in particular to a DNA sequencing method.

BACKGROUND OF THE INVENTION

DNA is a carrier of genetic information, and a specific order of the four base pairs therein is the essence of genetic information. Determination of the specific order of base pairs in DNA is called DNA sequencing, which has a fundamental role in revealing the mysteries of life, controlling genetic processes, promoting disease diagnosis, and improving medical technology. So far, two successive generations of sequencing technologies have been successfully developed and widely used. The first generation of sequencing technology based on dideoxy chain termination method has opened the door for humans to reveal genetic mysteries and laid the critical foundation for genetic engineering. The second generation of fluorescence detection method based on massively parallel synthesis utilizes PCR amplification and fluorescence detection on a basis of the first generation of sequencing technology, greatly improves the efficiency of sequencing, and makes great contributions to the completion of the first human genome sequencing. In spite of the well development of the previous two generations of sequencing technologies, there are still many drawbacks to be addressed, such as long time-consuming and high costs of PCR amplification, complexity and unstability of fluorescence labeling and detection process, etc. At the same time, with the deepening of human understanding of the nature of life and the continuous advancement of technical means in the medical field, personalized therapeutic regimen and molecular diagnosis have gradually become popular, which makes higher requirements on DNA sequencing. Therefore, how to perform DNA sequencing quickly, accurately and at low cost has become a hot research field.

At present, the relatively well-developed DNA sequencing technology is based on the nanopore-based electrical test platform. Even though commercial tester prototypes have emerged, the development of sequencing technology based on this method has been bottlenecked due to various defects such as difficulty in controlling DNA movement speed, low resolution of sequencing signals, and inaccuracy of sequencing, etc. With the continuous emergence of various new nano-materials and the continuous upgrading of micro-nano processing technology, the device platform with single-molecule detection capability has developed rapidly, providing continuous motivation and opportunities for the persistent advancement of DNA sequencing.

SUMMARY OF THE INVENTION

In order to solve the problem of the prior art, the first aspect of the present invention provides a single molecule device modified by DNA polymerase, wherein the single molecule device is a two-dimensional nanomaterial single molecule device, preferably a graphene-based single molecule device; or a low-dimensional nanomaterial single molecule device, preferably a one-dimensional nanomaterial single molecule device, more preferably a silicon nanowire single molecule device.

The term "single molecule device" as used herein may be any device in the prior art that is capable of responding to the change of a single molecule. That is to say, one skilled in the art can know whether a molecule has changed by detecting or observing the change in a corresponding single molecule device. Preferably, the present invention utilizes a single molecule device linked to DNA polymerase with graphene or silicon nanowires as electrodes. It can be known whether the conformation of the DNA polymerase has changed by detecting the change of current in the single molecule device.

The preparation process of the graphene-based single molecule device and the silicon nanowire single molecule device can be referred to the methods described in the document (Cao Y, Dong S, Liu S, He L, Gan L, Yu X, Steigerwald M L, Wu X, Liu Z, Guo X. Building high-throughput molecule junctions using indented graphene point contacts. Angew Chem Int Ed Engl. 2012 Dec. 3; 51(49): 12228-32.).

In one preferred embodiment of the first aspect of the present invention, the DNA polymerase has a linkage site to the single molecule device, and an amino acid residue providing the linkage site is located in a conformation changing region of the DNA polymerase.

As used herein, "an amino acid residue providing the linkage site is located in a conformation changing region of the DNA polymerase" means that the conformation of the DNA polymerase changes in a specific region everytime when the DNA polymerase accepts one dNTP during synthesis of DNA. Upon linkage of the DNA polymerase to the single molecule device, the change in the conformation of the DNA polymerase causes the change of the current in the single molecule device. In order to improve the sensitivity of subsequent DNA sequencing, the amino acid residue located in the conformation changing region of the DNA polymerase is preferably linked to the single molecule device. In addition, the change of the conformation in the DNA polymerase is not affected by the linkage of the amino acid residue providing a linkage site to the single molecule device.

In another preferred embodiment of the first aspect of the present invention, the DNA polymerase is linked to the single molecule device via only one linkage site. Preferably, the amino acid residue providing the linkage site occurs only once in the DNA polymerase.

As used herein, "the DNA polymerase is linked to the single molecule device via only one linkage site" means that only one amino acid residue is linked to the single molecule device.

As used herein, "the amino acid residue providing an linkage site occurs only once in the DNA polymerase" means that in order to ensure the only one linkage site, it is necessary to make the amino acid residue providing an linkage site occur only once in the DNA polymerase. If there is an identical amino acid or amino acid sequence at other positions in addition to the linkage site in the DNA polymerase, modification or mutation is required for the amino acid or amino acid sequence at other positions to prevent the amino acid or amino acid sequence at other positions from linking to the single molecule device. If there is no identical amino acid or amino acid sequence at other positions in addition to the single linkage site in the DNA polymerase, modification or mutation is not necessary for the amino acid or amino acid sequence at other positions. The modification or mutation refers to those performed in accordance with conventional knowledge of those skilled in the art without altering the activity or conformation changes of the DNA polymerase. For example, in one preferred embodiment of the present invention, the cysteine residue at position 907 from N terminal of the amino acid sequence shown in SEQ ID NO. 1 is substituted with any amino acid residue other than cysteine residue, preferably a serine residue.

In the context of the present invention, the DNA polymerase includes, but is not limited to, E. coli DNA polymerase I, II, III, IV, or V; or DNA polymerase α, β, γ, δ, or ε; preferably E. coli DNA polymerase I. Preferably, the amino acid sequence of E. coli DNA polymerase I is shown in SEQ ID NO. 1. Further preferably, the nucleotide sequence of E. coli DNA polymerase I is shown in SEQ ID NO. 2. In still another preferred embodiment of the first aspect of the present invention, the DNA polymerase is:

b1) a protein having the amino acid sequence shown in SEQ ID NO. 3, or a functional mutant thereof; or b2) a protein having the amino acid sequence shown in SEQ ID NO. 1, or a functional mutant thereof.

As used herein, the term "functional mutant" refers to a protein obtained by substitution and/or deletion and/or addition of one or more amino acid residues of the amino acid sequence, with retaining its original biological activity, i.e., guiding the synthesis of DNA.

In one preferred embodiment of the first aspect of the present invention, the functional mutant of the protein having the amino acid sequence shown in SEQ ID NO. 3 is a protein having the same function obtained by substitution and/or deletion and/or addition of one or more amino acid residues of the amino acid sequence shown in SEQ ID NO. 3.

In one preferred embodiment of the first aspect of the present invention, the functional mutant of the protein having the amino acid sequence shown in SEQ ID NO. 1 is a protein obtained by substitution of the cysteine residue at position 907 from N terminal of the amino acid sequence shown in SEQ ID NO. 1 with a non-cysteine residue, and substitution of the leucine residue at position 790 from N terminal of the amino acid sequence shown in SEQ ID NO. 1 with a cysteine residue; preferably, by substitution of the cysteine residue at position 907 from N terminal of the amino acid sequence shown in SEQ ID NO. 1 with a serine residue, and substitution of the leucine residue at position 790 from N terminal of the amino acid sequence shown in SEQ ID NO. 1 with a cysteine residue.

In one preferred embodiment of the first aspect of the present invention, when the DNA polymerase is linked to the single molecule device, the linkage site of the DNA polymerase is the cysteine at position 790 from N terminal of the amino acid sequence shown in SEQ ID NO. 1.

The DNA polymerase can be linked to the single molecule device using any linking manner known to those skilled in the art, as long as the activity and conformation changes of the DNA polymerase are maintained.

Preferably, the DNA polymerase and a graphene-based single molecule device can be linked as follows:

(1) preparing a graphene-based single molecule device;

(2) mixing the graphene-based single molecule device with p-phenylenediamine to obtain a graphene electrode having a terminal modified with amino;

(3) mixing 1,3,5-tris(4-carbonylphenyloxy)benzene with the graphene electrode having a terminal modified with amino to obtain an electrical circuit;

(4) mixing the electrical circuit with salt of sodium N-hydroxysulfosuccinimide (Sulfo-NHS) to obtain a Sulfo-NHS activated electrical circuit;

(5) mixing the Sulfo-NHS activated electrical circuit with N-(2-aminoethyl)maleimide hydrochloride to obtain a treated graphene-based single molecule device; and (6) mixing the treated graphene-based single molecule device with a DNA polymerase in an excess amount to obtain a graphene-based single molecule device modified by DNA polymerase.

Preferably, the DNA polymerase and a silicon nanowire single molecule device can be linked as follows:

(1) preparing the silicon nanowire single molecule device;

(2) mixing the silicon nanowire single molecule device with a HF solution to obtain an etched silicon nanowire single molecule device, wherein the HF solution is obtained by mixing 7 parts by volume of 40% (by mass) $NH_4F$ in an aqueous solution with 1 part by volume of 40% (by mass) HF in an aqueous solution, specifically a product from Beijing Chemical Works;

(3) mixing the etched silicon nanowire single molecule device with 10-undecynoic acid to obtain an electrical circuit;

(4) mixing the electrical circuit of step (3) with salt of sodium N-hydroxysulfosuccinimide (Sulfo-NHS) to obtain a Sulfo-NHS activated electrical circuit;

(5) mixing the Sulfo-NHS activated electrical circuit of step (4) with N-(2-aminoethyl)maleimide hydrochloride to obtain a treated silicon nanowire single molecule device; and (6) mixing the treated silicon nanowire single molecule device with DNA polymerase in an excess amount to obtain the silicon nanowire single molecule device modified by DNA polymerase.

In a particularly preferred embodiment of the first aspect of the present invention, the DNA polymerase in the single molecule device modified by DNA polymerase is contained in a microcavity, and preferably, the microcavity is made of polydimethylsiloxane.

Preferably, each DNA polymerase is contained in one microcavity.

In a specific embodiment of the first aspect of the present invention, the single molecule device modified by DNA polymerase is disposable.

In another specific embodiment of the first aspect of the present invention, the single molecule device modified by DNA polymerase is reusable.

A second aspect of the present invention provides a DNA sequencing method, comprising steps of:

(1) mixing a DNA to be sequenced with a sequencing primer and dNTP to obtain a reaction system; preferably, attaching a sequence paired with the sequencing primer to 3' terminal of the DNA to be sequenced;

(2) mixing the reaction system of step (1) with the single molecule device modified by DNA polymerase according to any one of claims 1 to 5;

(3) detecting an electrical signal of a source-drain current of the single molecule device modified by DNA polymerase over time during DNA synthesis; and
(4) analyzing the electrical signal to obtain a sequencing result.

In a preferred embodiment of the second aspect of the present invention, in step (1), the DNA to be sequenced is a single-stranded DNA or a double-stranded DNA, wherein if the DNA to be sequenced is a double-stranded DNA, the double-stranded DNA is firstly denatured and then mixed with the sequencing primer and dNTP.

In another preferred embodiment of the second aspect of the present invention, in step (1), a tag sequence having a nucleotide sequence reverse-complementary to the nucleotide sequence of the sequencing primer is attached to 3' terminal of the DNA to be sequenced; preferably, the nucleotide sequence of the sequencing primer is the sequence shown in SEQ ID NO. 4, and the nucleotide sequence of the tag sequence is the sequence at positions 51 to 68 from 5' terminal of the sequence shown in SEQ ID NO. 4.

In still another preferred embodiment of the second aspect of the present invention, in step (2), the DNA polymerase in the single molecule device modified by DNA polymerase is contained in a microcavity, preferably, the microcavity is made of polydimethylsiloxane; and the reaction system of step (1) is added into the microcavity.

In still another preferred embodiment of the second aspect of the present invention, wherein step (4) comprises:
statistically analyzing peak values of the source-drain current, and obtaining the sequencing result according to the base corresponding to each peak value; or statistically analyzing the high-state time corresponding to a high-state current and low-state time corresponding to a low-state current, calculating an average low-state time and an average high-state time, and obtaining the sequencing result according to the bases corresponding to each of the average low-state time and the average high-state time.

In one specific embodiment of the present invention, the sequencing method of the present invention is performed on the following DNAs to be sequenced, respectively:

5'-CCCCCCCCCCCCCCCCCCCCCCCCCCCCCCCCCCCCCCCCCC

CCCCC-3'(as shown in SEQ ID NO: 10);

5'-AAAAAAAAAAAAAAAAAAAAAAANAAAAAAAAAAAAAAAAA

AAAAAAAA-3'(as shown in SEQ ID NO: 11);

5'-GGGGGGGGGGGGGGGGGGGGGGGGGGGGGGGGGGGGGGGGGG

GGGGGGGG-3'(as shown in SEQ ID NO: 12);

5'-TTTTTTTTTTTTTTTTTTTTTTTTTTTTTTTTTTTTTTTTTT

TTTTT-3'(as shown in SEQ ID NO: 13); and

5'-TGCTAGCTGCTAATTGTCTCCATGTCATGTAGCTAGCTGTCACAG

T-3'(as shown in SEQ ID NO: 14).

The sequencing process specifically includes the following steps:
(1) attaching a tag sequence to 3' terminal of the DNA to be sequenced to form a DNA to be sequenced containing the tag sequence, the tag sequence having a nucleotide sequence reverse-complementary to the nucleotide sequence of a sequencing primer;

(2) mixing the DNA to be sequenced containing the tag sequence with the sequencing primer to form a product in a form of double strands at 5' terminal and a single strand at main part;
(3) mixing the product with dATP, dCTP, dTTP and dGTP, respectively, after completion of step (2) to obtain four systems, adding each system to the single molecule device modified by DNA polymerase, respectively, and reading electrical signals, wherein dNTP in the system having a significantly different electrical signal from other three systems is a1) or a2):
a1) a first nucleotide at 3' terminal of the DNA to be sequenced;
a2) a nucleotide of a first segment at 3' terminal of the DNA to be sequenced, the first segment being consisted of N nucleotides, and N being a natural number and greater than or equal to 2;
(4) mixing the product of the system having the significantly different electrical signal from other three systems in the previous step with dATP, dCTP, dTTP and dGTP, respectively, to obtain four systems, adding each system to the single molecule device modified by DNA polymerase, respectively, and reading electrical signals, wherein dNTP in the system having a significantly different electrical signal from other three systems is b1) or b2):
b1) a second nucleotide at 3' terminal of the DNA to be sequenced;
b2) a nucleotide of a second segment at 3' terminal of the DNA to be sequenced, the second segment consisting of M nucleotides, and M being a natural number and greater than or equal to 2;
(5) repeating step (4) until the sequencing result of the DNA to be sequenced is obtained.

In the above sequencing process, N is preferably 50 in the a2).

In the above sequencing process, M is preferably 50 in the b2).

In the above sequencing process, the DNA to be sequenced is a single-stranded DNA. When the DNA to be sequenced is a double-stranded DNA, it is required to be denatured firstly and then mixed with the sequencing primer.

The nucleotide sequence of the sequencing primer is preferably the sequence shown in SEQ ID NO. 4.

The nucleotide sequence of the tag sequence can be the sequence at positions 51 to 68 from 5' terminal of the sequence shown in SEQ ID NO. 4.

A third aspect of the present invention provides a kit for DNA sequencing, comprising a DNA polymerase and a single molecule device, wherein the single molecule device is a two-dimensional nanomaterial single molecule device, preferably a graphene-based single molecule device; or a low-dimensional nanomaterial single molecule device, preferably a one-dimensional nanomaterial single molecule device, more preferably a silicon nanowire single molecule device. In one preferred embodiment of the third aspect of the present invention, the DNA polymerase is:
b1) a protein having the amino acid sequence shown in SEQ ID NO. 3, or a functional mutant thereof; or
b2) a protein having the amino acid sequence shown in SEQ ID NO. 1, or a functional mutant thereof.

In another preferred embodiment of the third aspect of the present invention, wherein the DNA polymerase and the single molecule device are present in separate compartments, and linked on site when used; or the DNA polymerase is linked to the single molecule device; preferably the DNA polymerase has a linkage site to the single molecule device, and the amino acid residue providing the linkage site is located in a conformation changing region of the DNA polymerase; more preferably, the DNA polymerase is contained in a microcavity.

In still another preferred embodiment of the third aspect of the present invention, the kit further comprises a sequencing primer, dNTP and/or an instruction for use.

The method provided by the present invention can be used to perform DNA sequencing, and the sequencing result shows that DNA synthesis rate is substantially consistent with that described in the prior document (Tivoli J. Olsen, Yongki Choi, Patrick C. Sims, O. Tolga Gul, Brad L. Corso, Chengjun Dong, William A. Brown, Philip G. Collins and Gregory A. Weiss, Electronic Measurements of Single-Molecule Processing by DNA Polymerase I (Klenow Fragment), Journal of the American Chemical Society 2013, 135, 7855-7860). The DNA sequencing method provided by the present invention has a high value for application.

The single molecule device modified by DNA polymerase, the DNA sequencing method and the kit according to the present invention can be widely applied to DNA sequencing, and have at least the following advantages:

the sequencing rate is much faster than that of chemical sequencing methods, since the sequencing rate in the present invention depends on the inherent reaction rate of the DNA polymerase;

a very long sequence, such as having thousands of bases, can be detected by one reaction due to the inherent continuity of DNA polymerase, while the second generation sequencing can only detect hundreds of bases; and there is no base error introduced by amplification because of the absence of PCR amplification, resulting in a very high sequencing accuracy and resolution.

DESCRIPTION OF THE DRAWINGS

FIG. 1 (1) shows a schematic diagram of graphene electrode having nanogap on the graphene-based single molecule device, FIG. 1 (2) shows a schematic diagram of p-phenylenediamine, FIG. 1 (3) shows a schematic diagram of graphene electrode having a terminal modified with amino, FIG. 1 (4) shows a schematic diagram of 2, 1,3,5-tris(4-carbonylphenyloxy)benzene, FIG. 1 (5) shows a schematic diagram of partial structural formula of the electrical circuit, i.e., a device 5, FIG. 1 (6) shows a schematic diagram of Sulfo-NHS, FIG. 1 (7) shows a schematic diagram of partial structural formula of the Sulfo-NHS activated electrical circuit, i.e., a device 7, FIG. 1 (8) shows a schematic diagram of N-(2-aminoethyl)maleimide hydrochloride, FIG. 1 (9) shows a schematic diagram of partial structural formula of the treated graphene-based single molecule device, i.e., a device 9, FIG. 1 (10) shows a schematic diagram of reconstructed DNA polymerase I, FIG. 1 (11) shows a schematic diagram of partial structural formula of the graphene-based single molecule device modified by DNA polymerase, i.e., a device 11.

FIG. 2 (1) shows the conductivity of device 5 in FIG. 1 (5), indicating the successful preparation of a molecule device having carboxyl. FIG. 2 (2) shows the conductivity of device 7 in FIG. 1 (7), indicating the successful preparation of a molecule device having active ester. FIG. 2 (3) shows the conductivity of device 9 in FIG. 1 (9), indicating the successful preparation of a molecule device having maleimide. FIG. 2 (4) shows the conductivity of device 11 in FIG. 1 (11), indicating the successful preparation of a molecule device modified by DNA polymerase.

FIG. 6A shows a diagram of the kinetic data obtained in step 6 in section II of Example 1 after extending, wherein a corresponding high-state current and a low-state current were selected by Qub software, FIGS. 6B and 6C show the experimental results of the high-state time corresponding to the high-state current ($\tau_{hi}$) and the low-state time corresponding to the low-state current ($\tau_{low}$), respectively.

FIG. 14 (1) shows a schematic diagram of partial structure of the etched silicon nanowire single molecule device, FIG. 14 (2) shows a schematic diagram of 10-undecynoic acid, FIG. 14 (3) shows a schematic diagram of partial structure of the electrical circuit, FIG. 14 (4) shows a schematic diagram of Sulfo-NHS, FIG. 14 (5) shows a schematic diagram of partial structural formula of the Sulfo-NHS activated electrical circuit, FIG. 14 (6) shows a schematic diagram of N-(2-aminoethyl)maleimide hydrochloride, FIG. 14 (7) shows a schematic diagram of partial structural formula of the treated silicon nanowire single molecule device, FIG. 14 (8) shows a schematic diagram of reconstructed DNA polymerase I, FIG. 14 (9) shows a schematic diagram of partial structure of the silicon nanowire single molecule device modified by DNA polymerase.

DETAILED DESCRIPTION OF THE INVENTION

Figure 1:
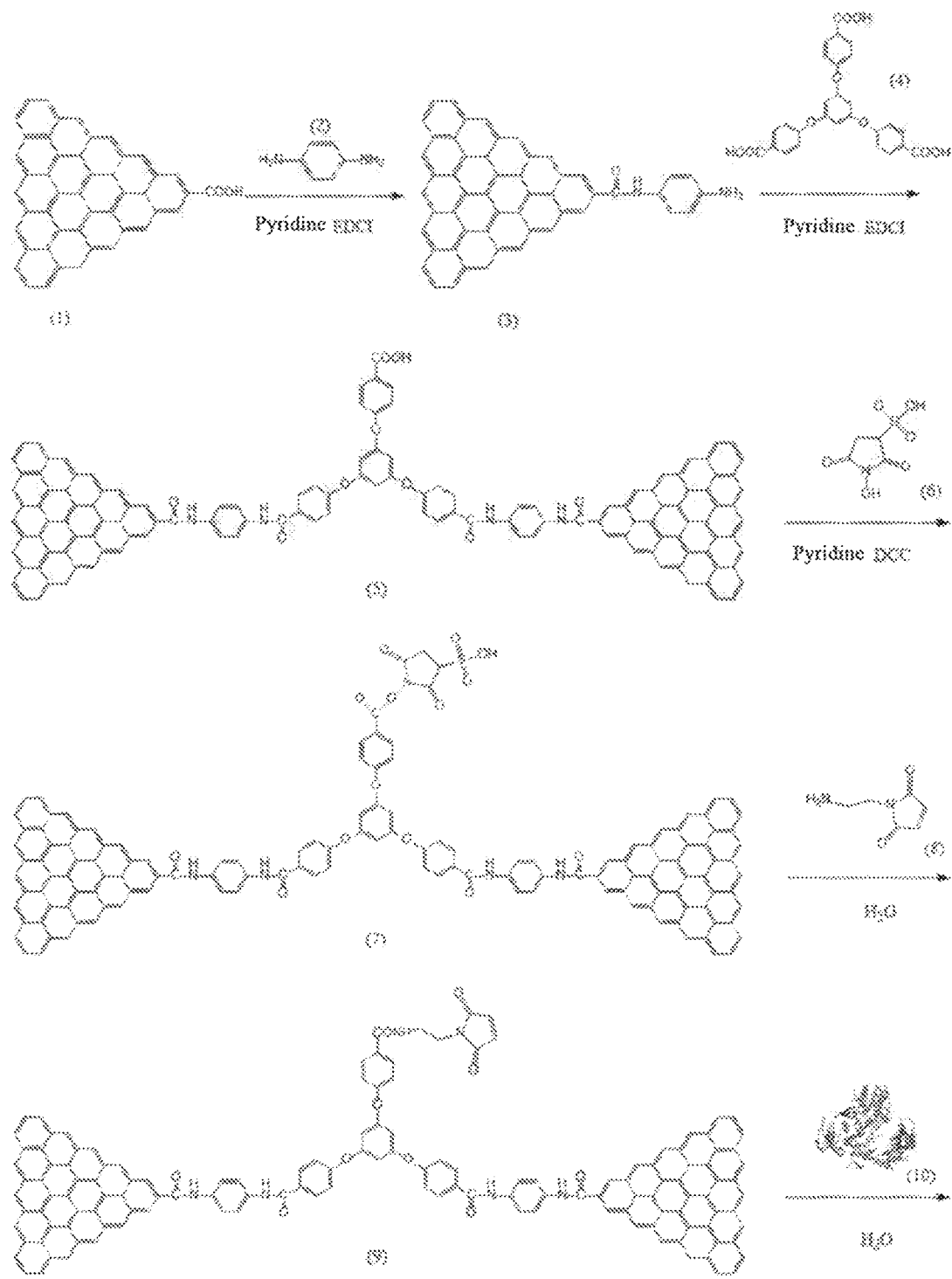
FIG. 1 is a flow diagram of the preparation of a graphene-based single molecule device modified by DNA polymerase.
Figure 1:
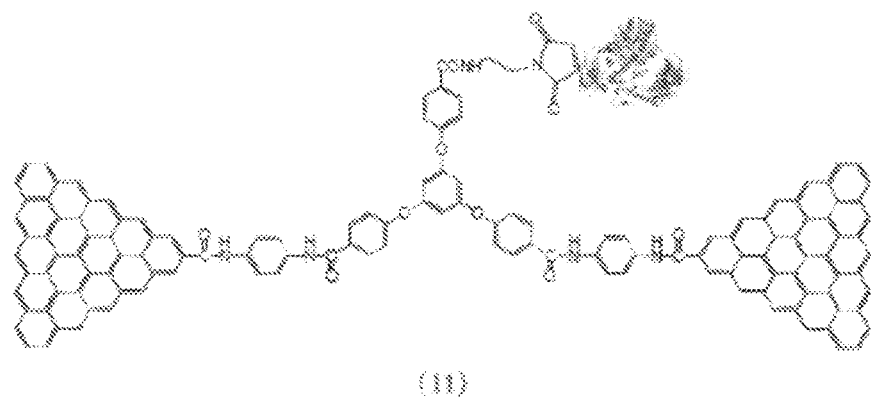

The present invention will be further described in detail below with reference to the drawings and examples, for the purpose of more clear illustration of the objects, technical solutions, and advantages of the present invention. It is obvious that the described examples are only a part rather than all of the examples of the invention. All other examples obtained by those skilled in the art based on the examples of the present invention without making creative efforts are fallen within the scope of the present invention.

The present invention is further described in detail with reference to the specific embodiments. The examples are given only to illustrate the present invention and are not intended to limit the scope of the present invention.

The experimental methods in the following examples are conventional methods in the art, unless otherwise specified.

The materials, reagents, etc. used in the following examples are commercially available, unless otherwise specified.

DTT buffer is pH 7.8, 10 mM Tris-HCl buffer containing 50 mM NaCl, 10 mM $MgCl_2$ and 1 mM DTT.

HF solution is obtained by mixing 7 parts by volume of 40% (by mass) $NH_4F$ in an aqueous solution with 1 part by volume of 40% (by mass) HF in an aqueous solution, which is a product from Beijing Chemical Works.

```
Single-stranded DNA molecule I:
5'-(C)50ACTGGCCGTCGTTTTACA-3'(as shown in SEQ

ID NO. 4).

Single-stranded DNA molecule II:
5'-TGTAAAACGACGGCCAGT-3'(as shown in SEQ ID NO.

5).

Single-stranded DNA molecule III:
5'-(A)50ACTGGCCGTCGTTTTACA-3'(as shown in SEQ

ID NO. 6).

Single-stranded DNA molecule IV:
5'-(G)50ACTGGCCGTCGTTTTACA-3'(as shown in SEQ

ID NO. 7).

Single-stranded DNA molecule V:
5'-(T)50ACTGGCCGTCGTTTTACA-3'(as shown in SEQ
```

-continued

```
ID NO. 8).

Single-stranded DNA molecule VI:
5'-TGCTAGCTGCTAATTGTCTCCATGTCATGTAGCTAGCTGTCACAG TACTGGCCGTCGTTTTACA-3' (as shown in SEQ ID

NO. 9).
```

The template strand C is prepared as follows. Single-stranded DNA molecule I and single-stranded DNA molecule II are artificially synthesized. Then 10 μL of single-stranded DNA molecule I (the concentration of single-stranded DNA molecule I is 10 μM), 10 μL of single-stranded DNA molecule II (the concentration of single-stranded DNA molecule II is 10 μM), and 980 μL of DTT buffer are mixed, heated at 70° C. for 1 h, and naturally cooled to room temperature to obtain a template strand C (in a form of double strands at 5' terminal and a single strand at main part). The template strand C needs to be prepared 3 hours before a kinetic test.

The template strand A is prepared as follows. Single-stranded DNA molecule III and single-stranded DNA molecule II are artificially synthesized. Then 10 μL of single-stranded DNA molecule III (the concentration of single-stranded DNA molecule III is 10 μM), 10 μL of single-stranded DNA molecule II (the concentration of single-stranded DNA molecule II is 10 μM), and 980 μL of DTT buffer are mixed, heated at 70° C. for 1 h, and naturally cooled to room temperature to obtain a template strand A (in a form of double strands at 5' terminal and a single strand at main part). The template strand A needs to be prepared 3 hours before a kinetic test.

The template strand G is prepared as follows. Single-stranded DNA molecule IV and single-stranded DNA molecule II are artificially synthesized. Then 10 μL of single-stranded DNA molecule IV (the concentration of single-stranded DNA molecule IV is 10 μM), 10 μL of single-stranded DNA molecule II (the concentration of single-stranded DNA molecule II is 10 μM), and 980 μL of DTT buffer are mixed, heated at 70° C. for 1 h, and naturally cooled to room temperature to obtain a template strand G (in a form of double strands at 5' terminal and a single strand at main part). The template strand G needs to be prepared 3 hours before a kinetic test.

The template strand T is prepared as follows. Single-stranded DNA molecule V and single-stranded DNA molecule II are artificially synthesized. Then 10 μL of single-stranded DNA molecule V (the concentration of single-stranded DNA molecule V is 10 μM), 10 μL of single-stranded DNA molecule II (the concentration of single-stranded DNA molecule II is 10 μM), and 980 μL of DTT buffer are mixed, heated at 70° C. for 1 h, and naturally cooled to room temperature to obtain a template strand T (in a form of double strands at 5' terminal and a single strand at main part). The template strand T needs to be prepared 3 hours before a kinetic test.

The random strand is prepared as follows. Single-stranded DNA molecule VI and single-stranded DNA molecule II are artificially synthesized. Then 10 μL of single-stranded DNA molecule VI (the concentration of single-stranded DNA molecule VI is 10 μM), 10 μL of single-stranded DNA molecule II (the concentration of single-stranded DNA molecule II is 10 μM), and 980 μL of DTT buffer are mixed, heated at 70° C. for 1 h, and naturally cooled to room temperature to obtain a random strand (in a form of double strands at 5' terminal and a single strand at main part). The random strand needs to be prepared 3 hours before a kinetic test.

The low-resolution probe station consists of a semiconductor parameter meter (Agilent, 4155C) and a probe station (Karl Suess, PM5).

The high-resolution probe station consists of two core components: a preamplifier (Digital Instruments, DL1211) and a lock-in amplifier (Zurich Instruments, HF2LI).

1,3,5-tris(4-carbonylphenyloxy)benzene is a product from Jinan Henghua Technology Co., Ltd.

dATP solution is obtained by dissolving dATP in DTT buffer. dCTP solution is obtained by dissolving dCTP in DTT buffer. dTTP solution is obtained by dissolving dTTP in DTT buffer. dGTP solution is obtained by dissolving dGTP in DTT buffer. dATP, dCTP, dTTP, and dGTP are all products from Beijing SBS Genetech Co., Ltd.

Example 1. DNA Sequencing Using a Graphene-Based Single Molecule Device Modified by DNA Polymerase I. Preparation of a Graphene-Based Single Molecule Device Modified by DNA Polymerase 1. Preparation of a Graphene-Based Single Molecule Device The preparation process of the graphene-based single molecule device can be referred to the following document: Cao Y, Dong S, Liu S, He L, Gan L, Yu X, Steigerwald M L, Wu X, Liu Z, Guo X. Building high-throughput molecular junctions using indented graphene point contacts. Angew Chem Int Ed Engl. 2012 Dec. 3; 51(49): 12228-32. There is a graphene electrode having nanogap on the graphene-based single molecule device (hereinafter referred to as a graphene electrode, the structural formula thereof is shown in FIG. 1 (1)).

The following steps 2 to 7 were performed according to the methods reported in the documents: Yang Cao, Shaohua Dong, Song Liu, Li He, Lin Gan, Xiaoming Yu, Michael L. Steigerwald, Xiaosong Wu, Zhongfan Liu and Xuefeng Guo*, Building High-Throughput Molecular Junctions Using Indented Graphene Point Contacts, Angew. Chem. Int. Ed. 2012, 51, 12228; and Xuefeng Guo, Alon Gorodetsky, Jacqueline K. Barton, James Hone, Colin Nuckolls*, Conductivity of a single DNA duplex bridging a carbon nanotube gap, Nat. Nanotechnol. 2008, 3, 163.

2. Terminal Modification with Amino

After completion of step 1, the graphene-based single molecule device was mixed with p-phenylenediamine (see FIG. 1 (2)) to modify the terminal of the graphene electrode with amino. The structural formula of the graphene electrode having a terminal modified with amino is shown in FIG. 1 (3).

3. Construction of an Electrical Circuit

After completion of step 2, 1,3,5-tris(4-carbonylphenyloxy)benzene (see FIG. 1 (4)) was mixed with the graphene electrode having a terminal modified with amino to obtain an electrical circuit. The electrical properties of the electrical circuit were detected using a low-resolution probe station. The results are shown in the upper left panel of FIG. 2. The partial structural formula of the electrical circuit is shown in FIG. 1 (5).

4. Sulfo-NHS Activation

After completion of step 3, the electrical circuit was mixed with salt of sodium N-hydroxysulfosuccinimide (Sulfo-NHS, see FIG. 1 (6)) to obtain a Sulfo-NHS activated electrical circuit. The electrical properties of the Sulfo-NHS activated electrical circuit were detected using a low-resolution probe station. The results are shown in the upper right panel of FIG. 2. The partial structural formula of the Sulfo-NHS activated electrical circuit is shown in FIG. 1 (7).

5. Acquisition of a Treated Graphene-Based Single Molecule Device

After completion of step 4, the Sulfo-NHS activated electrical circuit was mixed with N-(2-aminoethyl)maleimide hydrochloride (see FIG. 1 (8)) to obtain a treated graphene-based single molecule device. The partial structural formula of the treated graphene-based single molecule device is shown in FIG. 1 (9). The electrical properties of the treated graphene-based single molecule device were detected using a low-resolution probe station. The results are shown in the lower left panel of FIG. 2.

Figure 2:
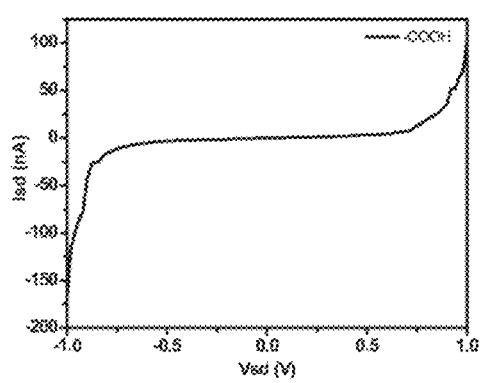
FIG. 2 shows the electrical properties detected by a low-resolution probe station; wherein Vsd represents the source-drain bias voltage and Isd represents the source-drain current.
Figure 2:
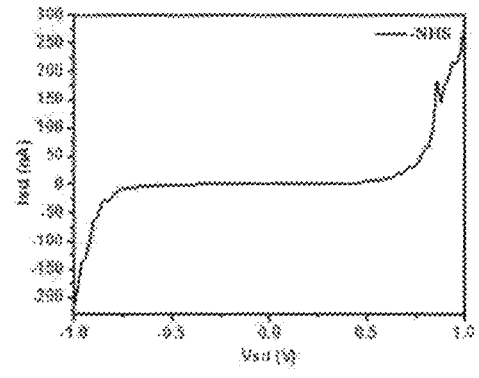
Figure 2:
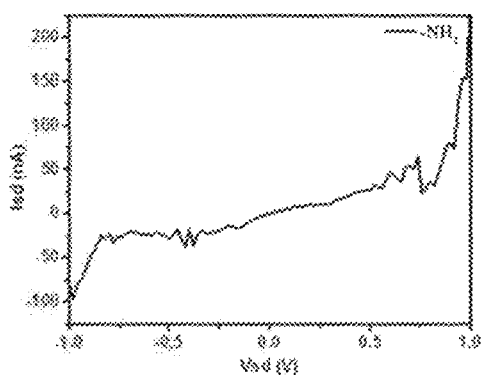
Figure 2:
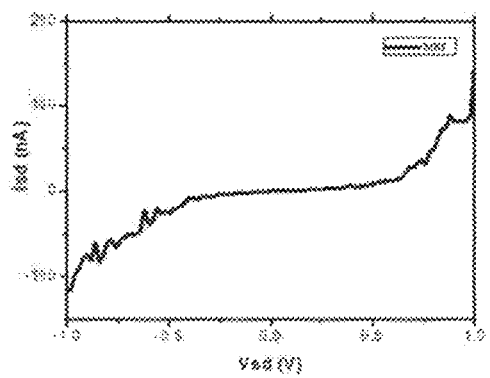

FIG. 2 (1) shows the conductivity of device 5 in FIG. 1 (5), indicating the successful preparation of a molecule device having carboxyl. FIG. 2 (2) shows the conductivity of device 7 in FIG. 1 (7), indicating the successful preparation of a molecule device having active ester. FIG. 2 (3) shows the conductivity of device 9 in FIG. 1 (9), indicating the successful preparation of a molecule device having maleimide. FIG. 2 (4) shows the conductivity of device 11 in FIG. 1 (11), indicating the successful preparation of a molecule device modified by DNA polymerase.

6. Reconstruction of *E. coli* DNA Polymerase I (1) Reconstruction Principle

The amino acid sequence and nucleotide sequence of *E. coli* DNA polymerase I (hereinafter referred to as DNA polymerase I) are shown in SEQ ID NO. 1 and SEQ ID NO. 2, respectively. The reconstructed DNA polymerase I is required to have the following characteristics simultaneously: (1) it possess the biological activity of DNA polymerase I, that is, guiding the synthesis of DNA; (2) it can be linked to a treated graphene-based single molecule device via only one linkage site provided by an amino acid residue (named donor amino acid residue), which should be located in a conformation changing region of the reconstructed DNA polymerase I (in order to improve sensitivity of subsequent DNA sequencing); and (3) the amino acid species corresponding to the donor amino acid residue and to the amino acid residue not providing a linkage site (named non-donor amino acid residue) are different.

(2) Acquisition of Reconstructed DNA Polymerase I

Reconstructed DNA polymerase I was obtained by extensive experiments using the methods reported in the document (Tivoli J. Olsen, Yongki Choi, Patrick C. Sims, O. Tolga Gul, Brad L. Corso, Chengjun Dong, William A. Brown, Philip G. Collins and Gregory A. Weiss, Electronic Measurements of Single-Molecule Processing by DNA Polymerase I (Klenow Fragment), Journal of the American Chemical Society 2013, 135, 7855-7860). The reconstructed DNA polymerase I (amino acid sequence thereof is shown in SEQ ID NO. 3) was prepared by Sangon Biotech (Shanghai) Co., Ltd. The reconstructed DNA polymerase I has an amino acid sequence in which a cysteine residue at position 907 from N terminal of DNA polymerase I (amino acid sequence thereof is shown in SEQ ID NO. 1) is substituted with a serine residue, and a leucine residue at position 790 from N terminal of DNA polymerase I is substituted with a cysteine residue. The amino acid residue at position 790 from N terminal of SEQ ID NO. 3 is located in a conformation changing region.

Figure 3:
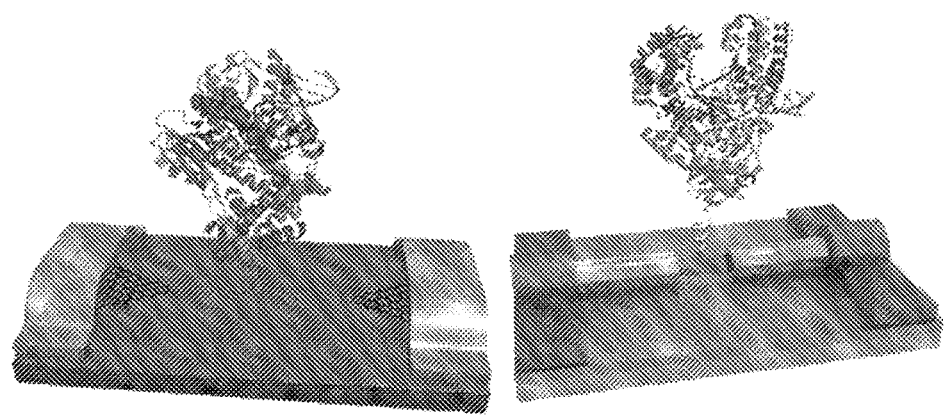
FIG. 3 is a schematic diagram of a graphene-based single molecule device modified by DNA polymerase and a silicon nanowire single molecule device modified by DNA polymerase.
Figure 4:
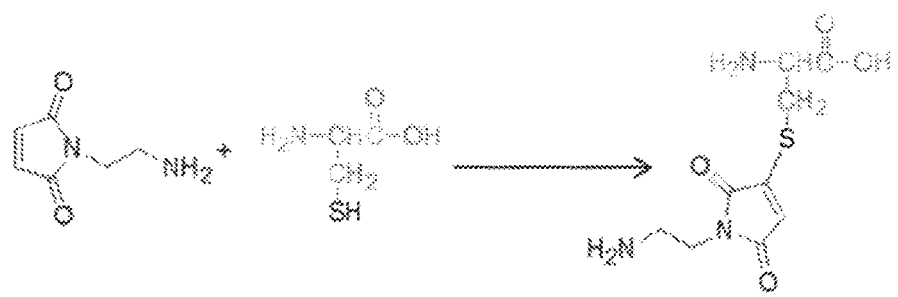
FIG. 4 is a reaction formula in which cysteine is chemically reacted with a treated graphene-based single molecule device.

7. Preparation of a Graphene-Based Single Molecule Device Modified by DNA Polymerase After completion of step 6, the treated graphene-based single molecule device was mixed with the reconstructed DNA polymerase I in an excess amount (see FIG. 1 (10)), to obtain a graphene-based single molecule device modified by DNA polymerase (the left panel of FIG. 3). The partial structural formula of the graphene-based single molecule device modified by DNA polymerase is shown in FIG. 1 (11). The electrical properties of the graphene-based single molecule device modified by DNA polymerase were detected using a low-resolution probe station. The results are shown in the lower right panel of FIG. 2. The reaction formula in which cysteine in the reconstructed DNA polymerase I is reacted with the treated graphene-based single molecule device is shown in FIG. 4.

The prepared graphene-based single molecule device modified by DNA polymerase was placed on a low-resolution probe station to observe conductivity. The graphene-based single molecule device having conductivity was selected for the following experiments. The specific steps refer to the methods reported in the document: Tivoli J. Olsen, Yongki Choi, Patrick C. Sims, O. Tolga Gul, Brad L. Corso, Chengjun Dong, William A. Brown, Philip G. Collins and Gregory A. Weiss, Electronic Measurements of Single-Molecule Processing by DNA polymerase I (Klenow Fragment), Journal of the American Chemical Society 2013, 135, 7855-7860.

II. DNA Sequencing of Template Stand C Using the DNA Polymerase-Modified Graphene-Based Single Molecule Device 1. The graphene-based single molecule device modified by DNA polymerase was taken, and the reconstructed DNA polymerase I was contained in a 40 µL of microcavity (made of polydimethylsiloxane (PDMS)), to obtain a graphene-based single molecule device containing the microcavity.

Figure 5:
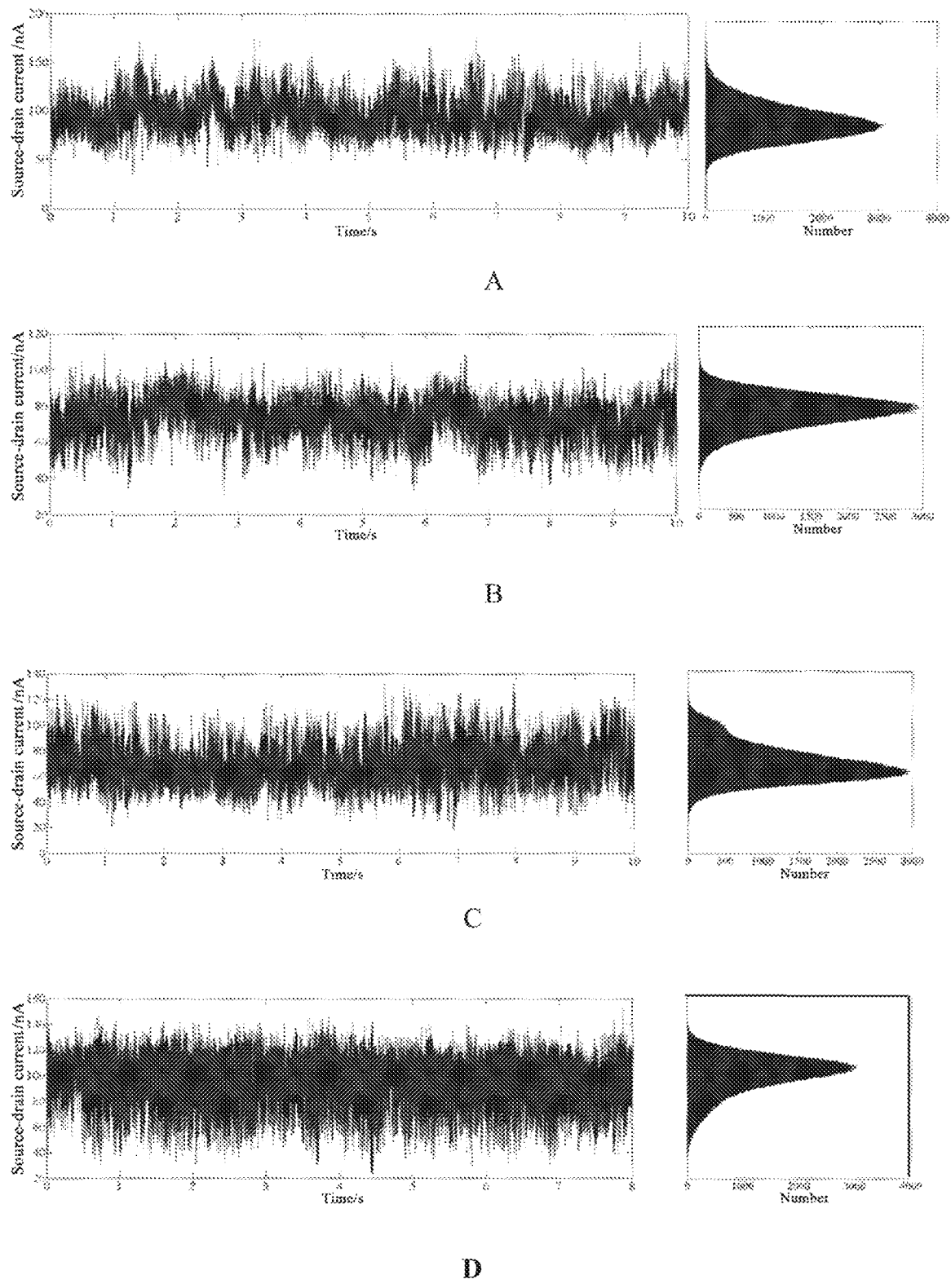
FIG. 5 is kinetic data and peak statistical results obtained from DNA sequencing of template strand C using a graphene-based single molecule device modified by DNA polymerase. The left panel and the right panel of FIG. 5A show the experimental results of the kinetic test and peak statistics of the graphene-based single molecule device containing the microcavity, respectively. The left panel and the right panel of FIG. 5B show the graphene-based single molecule device containing the microcavity with 10 µL of DTT buffer, respectively. The left panel and the right panel of FIG. 5C show the graphene-based single molecule device containing the microcavity with 100 nM template strand C in 30 µL of DTT buffer, respectively. The left panel and the right panel of FIG. 5D show the graphene-based single molecule device containing the microcavity with 100 nM template strand C in 30 µL of DTT buffer, 5 µL of dATP solution, 5 µL of dTTP solution and 5 µL of dCTP solution, respectively. The left panel and the right panel of FIG. 5E show the graphene-based single molecule device containing the microcavity with 100 nM template strand C in 30 µL of DTT buffer and 5 µL of dGTP solution, respectively.
Figure 5:
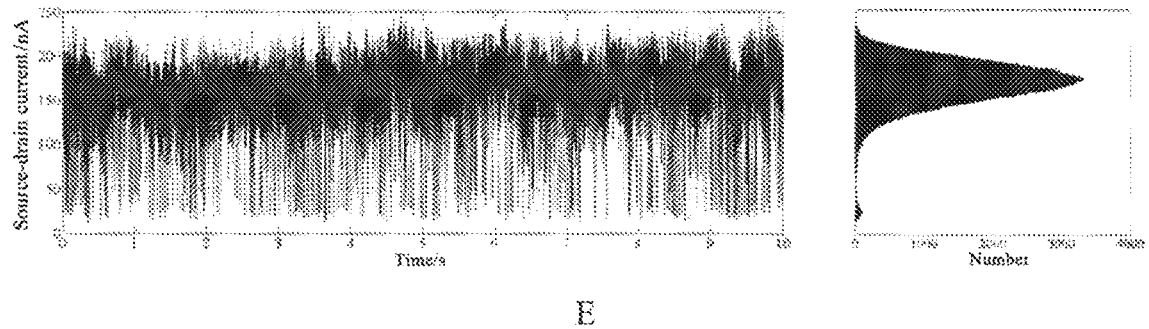

2. After completion of step 1, the graphene-based single molecule device containing the microcavity was placed on a high-resolution probe station, and sampled for 5 minutes for a kinetic test (i.e., testing changes of source-drain current over time). The experimental results are shown in the left panel of FIG. 5A. The preliminary peak statistics were then performed using MatLab software. The experimental results are shown in the right panel of FIG. 5A, indicating that no oscillation signal of DNA synthesis was observed in the absence of sample.

3. After completion of step 1, the microcavity in the graphene-based single molecule device containing the same was added with 10 µL of DTT buffer, and sampled for 5 minutes for a kinetic test (i.e., testing changes of source-drain current over time). The experimental results are shown in the left panel of FIG. 5B. The preliminary peak statistics were then performed using MatLab software. The experimental results are shown in the right panel of FIG. 5B, indicating that no oscillation signal of DNA synthesis was observed in the presence of buffer alone and in the absence of sample.

4. After completion of step 1, the microcavity in the graphene-based single molecule device containing the same was added with 100 nM template strand C in 30 µL of DTT buffer, and sampled for 5 minutes for a kinetic test (i.e., testing changes of source-drain current over time). The experimental results are shown in the left panel of FIG. 5C. The preliminary peak statistics were then performed using MatLab software. The experimental results are shown in the right panel of FIG. 5C, indicating that no oscillation signal of DNA synthesis was observed in the presence of template strand and buffer and in the absence of sample.

5. After completion of step 1, the microcavity in the graphene-based single molecule device containing the same was added with 100 nM template strand C in 30 µL of DTT buffer, 5 µL of dATP solution (at a concentration of 5 µM), 5 µL of dTTP solution (at a concentration of 5 µM) and 5 µL of dCTP solution (at a concentration of 5 µM), and sampled for 10 minutes for a kinetic test (i.e., testing changes of source-drain current over time). The experimental results are shown in the left panel of FIG. 5D. The preliminary peak statistics were then performed using MatLab software. The experimental results are shown in the right panel of FIG. 5D, indicating that no oscillation signal of DNA synthesis was observed in the case that template strand, nucleic acid molecules, and buffer are present but the bases are not matched.

6. After completion of step 1, the microcavity in the graphene-based single molecule device containing the same was added with 100 nM template strand C in 30 µL of DTT buffer and 5 µL of dGTP solution (at a concentration of 5 M), and sampled for 10 minutes to test changes of source-drain current over time during DNA synthesis performed by DNA polymerase, i.e., the kinetic data during DNA polymerization performed by DNA polymerase. The experimental results are shown in the left panel of FIG. 5E. The preliminary peak statistics were then performed using MatLab software. The experimental results are shown in the right panel of FIG. 5E, indicating that an oscillation signal of DNA synthesis was observed in the case that template strand, nucleic acid molecules, and buffer are present and the bases are matched.

Figure 6:
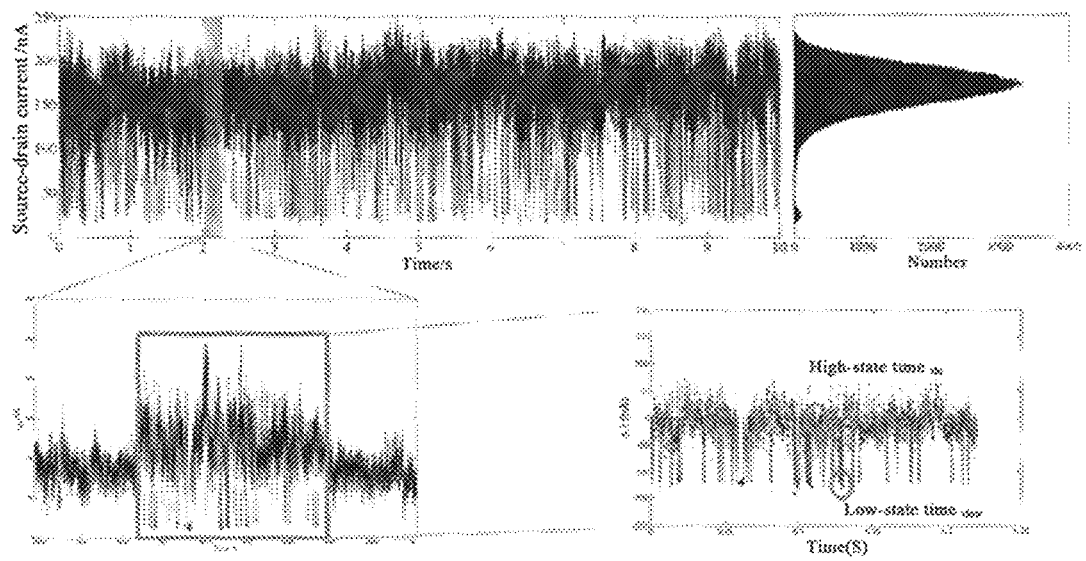
FIG. 6 is statistical analysis results of high-state and low-state time obtained from DNA sequencing of template strand C using a graphene-based single molecule device modified by DNA polymerase.
Figure 6:
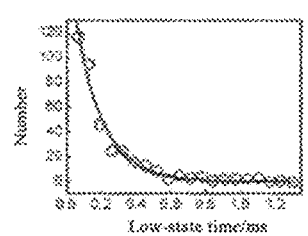
Figure 6:
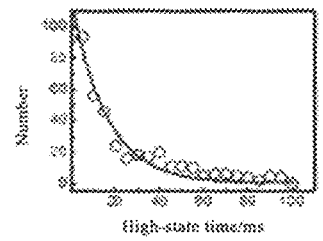

The results show that the kinetic data in step 6 are essentially different from those in other control experiments apparently, that is, when template strand C and the deoxynucleotide matching with it are present in the system, the kinetic data of the system can be different from those of other four groups of control experiments. 7. The kinetic data obtained in step 6 were extended, and a corresponding high-state current (i.e., high current) and a low-state current (i.e., low current) were selected by Qub software (FIG. 6A). A high-state time corresponding to the high-state current ($\tau_{hi}$) and a low-state time corresponding to the low-state current ($\tau_{low}$) were statistically analyzed. The experimental results are shown in FIGS. 6B and 6C, respectively. According to an average low-state time and an average high-state time, the rate of DNA synthesis in this system was calculated to be 62.62 dGTP nucleotides per second (see Table 1) by counting the number of the low-state, which is substantially consistent with the synthesis rate described in the previous document (Tivoli J. Olsen, Yongki Choi, Patrick C. Sims, O. Tolga Gul, Brad L. Corso, Chengjun Dong, William A. Brown, Philip G. Collins and Gregory A. Weiss, Electronic Measurements of Single-Molecule Processing by DNA Polymerase I (Klenow Fragment), Journal of the American Chemical Society 2013, 135, 7855-7860). It should be noted that the average mentioned herein is not a linear average simply, but a Poisson average based on the exponential distribution. The specific calculation process is performed by MatLab software.

TABLE 1

|  | Template strand C | Template strand G | Template strand T | Template strand A |
|---|---|---|---|---|
| $\tau_{low}$ (ms) | 0.156 | 0.122 | 0.710 | 2.825 |
| $\tau_{hi}$ (ms) | 15.813 | 6.823 | 3.585 | 3.575 |
| Synthesis rate (nucleotides/second) | 62.62 | 143.99 | 232.83 | 156.25 |

Figure 7:
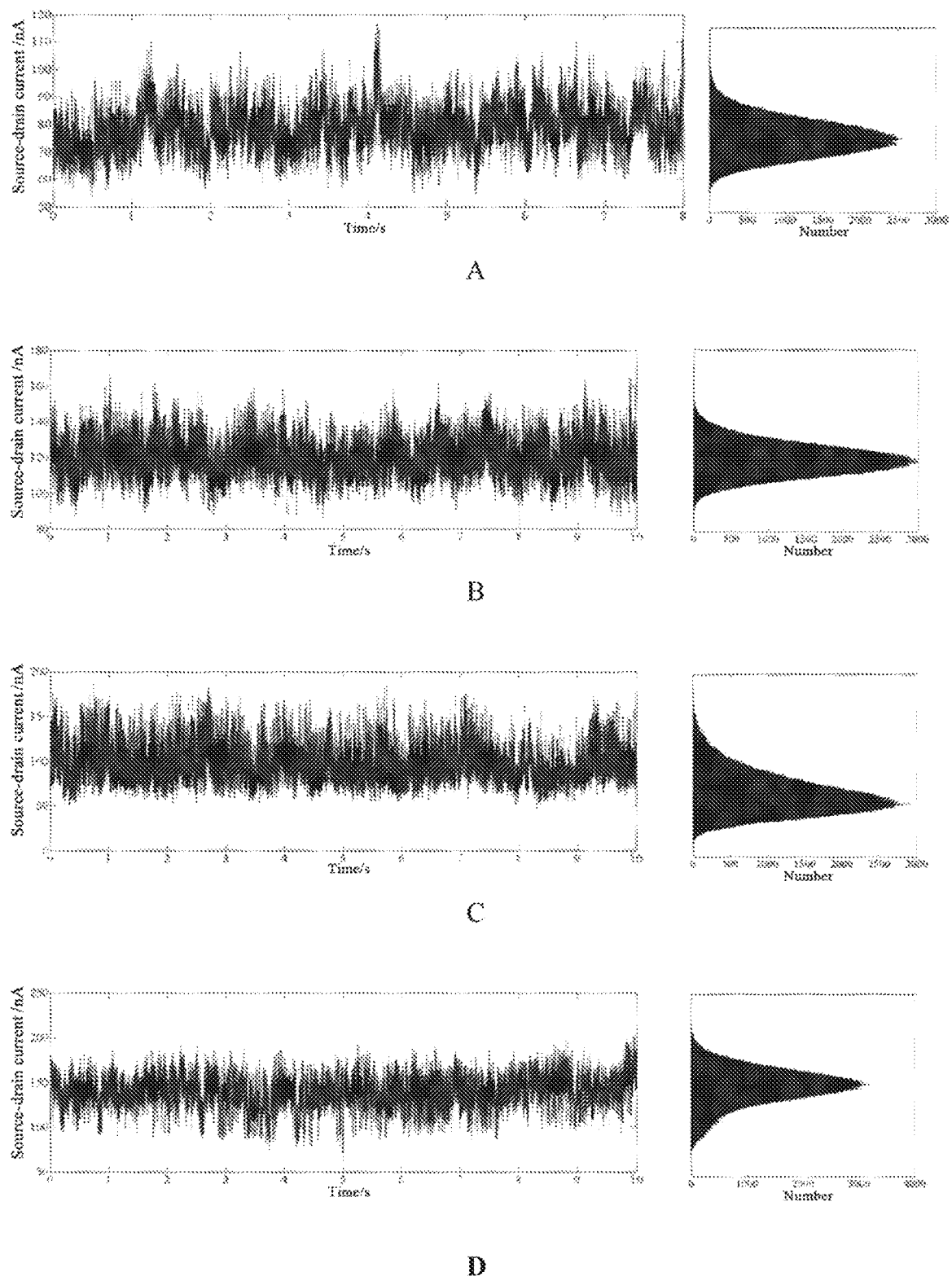
FIG. 7 is kinetic data and peak statistical results obtained from DNA sequencing of template strand A using a graphene-based single molecule device modified by DNA polymerase. The left panel and the right panel of FIG. 7A show the experimental results of the kinetic test and peak statistics by the method being the same as that in step 2 in section II of Example 1, respectively. The left panel and the right panel of FIG. 7B show the experimental results of the kinetic test and peak statistics by the method being the same as that in step 3 in section II of Example 1, respectively. The left panel and the right panel of FIG. 7C show the experimental results of the kinetic test and peak statistics by the method being the same as that in step 4 in section II of Example 1, respectively. The left panel and the right panel of FIG. 7D show the experimental results of the kinetic test and peak statistics of the graphene-based single molecule device containing the microcavity with 100 nM template strand A in 30 µL of DTT buffer, 5 µL of dATP solution, 5 µL of dGTP solution and 5 µL of dCTP solution, respectively. The left panel and the right panel of FIG. 7E show the experimental results of the kinetic test and peak statistics of the graphene-based single molecule device containing the microcavity with 100 nM template strand A in 30 μL of DTT buffer and 5 μL of dTTP solution, respectively.
Figure 7:
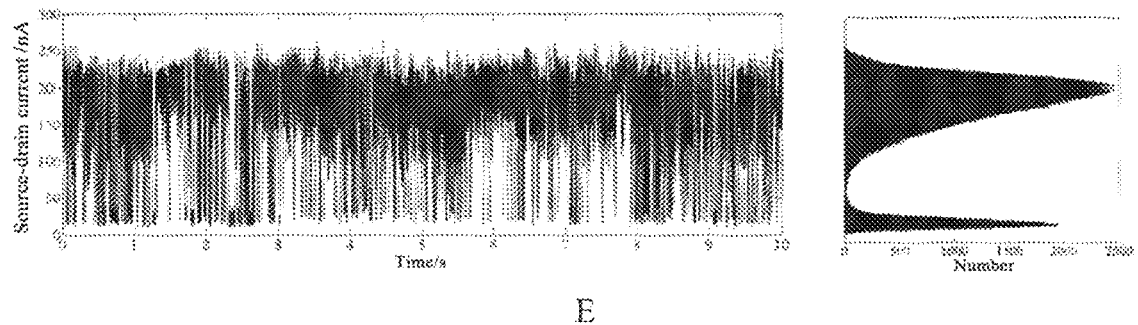

III. DNA sequencing of template stand A using a graphene-based single molecule device modified by DNA polymerase 1. The method is the same as that in step II-1.
2. The method is the same as that in step II-2. The experimental results of the kinetic test are shown in the left panel of FIG. 7A. The experimental results of peak statistics are shown in the right panel of FIG. 7A, indicating that no oscillation signal of DNA synthesis was observed in the absence of sample.
3. The method is the same as that in step II-3. The experimental results of the kinetic test are shown in the left panel of FIG. 7B. The experimental results of peak statistics are shown in the right panel of FIG. 7B, indicating that no oscillation signal of DNA synthesis was observed in the presence of buffer alone and in the absence of sample.
4. The method is the same as that in step II-4, except that the template strand C is substituted with a template strand A. The experimental results of the kinetic test are shown in the left panel of FIG. 7C. The experimental results of peak statistics are shown in the right panel of FIG. 7C, indicating that no oscillation signal of DNA synthesis was observed in the presence of template strand and buffer and in the absence of sample.
5. After completion of step 1, the microcavity in the graphene-based single molecule device containing the same was added with 100 nM template strand A in 30 µL of DTT buffer, 5 µL of dATP solution (at a concentration of 5 µM), 5 µL of dGTP solution (at a concentration of 5 µM) and 5 µL of dCTP solution (at a concentration of 5 µM), and sampled for 10 minutes for a kinetic test (i.e., testing changes of source-drain current over time). The experimental results are shown in the left panel of FIG. 7D. The preliminary peak statistics were then performed using MatLab software. The experimental results are shown in the right panel of FIG. 7D, indicating that no oscillation signal of DNA synthesis was observed in the case that template strand, nucleic acid molecules, and buffer are present but the bases are not matched.
6. After completion of step 1, the microcavity in the graphene-based single molecule device containing the same was added with 100 nM template strand A in 30 µL of DTT buffer and 5 µL of dTTP solution (at a concentration of 5 µM), and sampled for 10 minutes to test changes of source-drain current over time during DNA synthesis performed by DNA polymerase, i.e., the kinetic data during DNA polymerization performed by DNA polymerase. The experimental results are shown in the left panel of FIG. 7E. The preliminary peak statistics were then performed using MatLab software. The experimental results are shown in the right panel of FIG. 7E, indicating that the oscillation signal of DNA synthesis was observed in the case that template strand, nucleic acid molecules, and buffer are present and the bases are matched.

Figure 8:
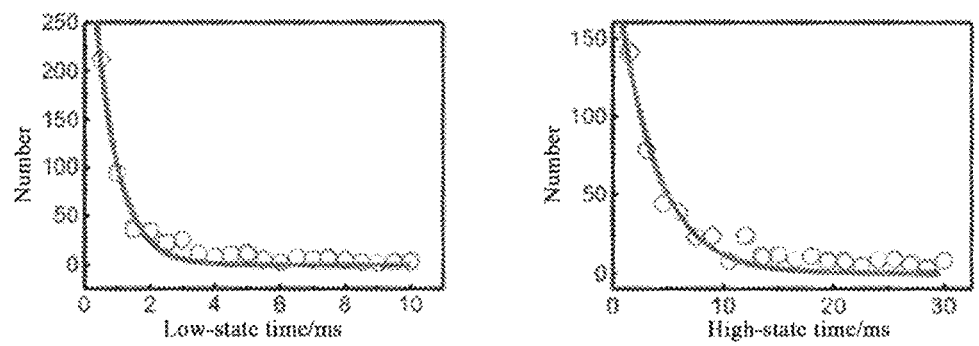
FIG. 8 is statistical analysis results of high-state and low-state time obtained from DNA sequencing of template strand A using a graphene-based single molecule device modified by DNA polymerase.

The results show that the kinetic data in step 6 are essentially different from those in other control experiments apparently, that is, when template strand A and the deoxynucleotide matching with it are present in the system, the kinetic data of the system can be different from those of other four groups of control experiments. 7. According to the method of step II-7, a high-state time corresponding to a high-state current ($\tau_{hi}$) and a low-state time corresponding to a low-state current ($\tau_{low}$) were statistically analyzed. The experimental results are shown in FIG. 8 (the left panel shows the low-state time, and the right panel shows the high-state time). The rate of DNA synthesis in this system was calculated to be 156.25 dTTP nucleotides per second (see Table 1) according to an average low-state time and an average high-state time, which is substantially consistent with the synthesis rate described in the previous document (Tivoli J. Olsen, Yongki Choi, Patrick C. Sims, O. Tolga Gul, Brad L. Corso, Chengjun Dong, William A. Brown, Philip G. Collins and Gregory A. Weiss, Electronic Measurements of Single-Molecule Processing by DNA Polymerase I (Klenow Fragment), Journal of the American Chemical Society 2013, 135, 7855-7860).

Figure 9:
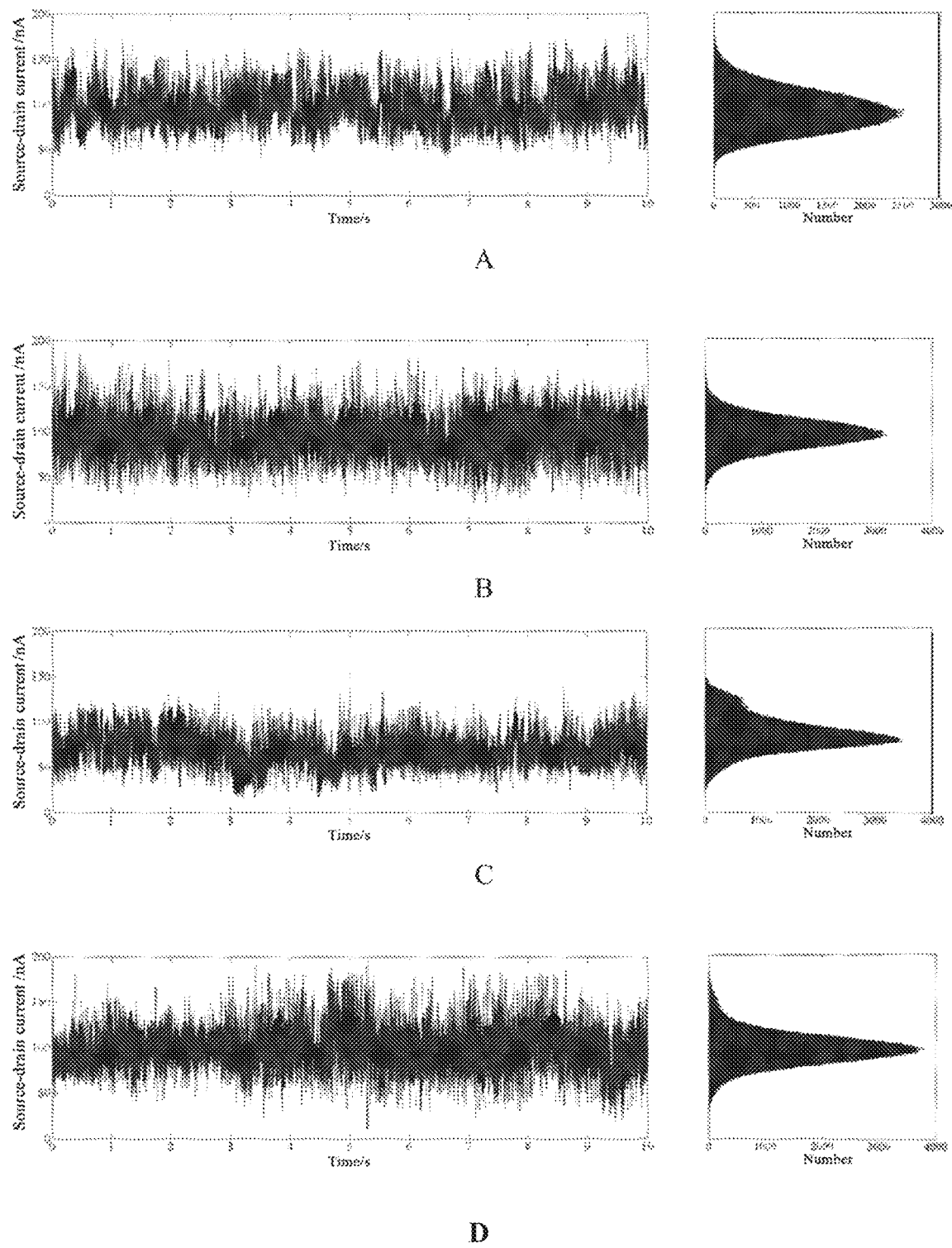
FIG. 9 is kinetic data and peak statistical results obtained from DNA sequencing of template strand G using a graphene-based single molecule device modified by DNA polymerase. The left panel and the right panel of FIG. 9A show the experimental results of the kinetic test and peak statistics by the method being the same as that in step 2 in section II of Example 1, respectively. The left panel and the right panel of FIG. 9B show the experimental results of the kinetic test and peak statistics by the method being the same as that in step 3 in section II of Example 1, respectively. The left panel and the right panel of FIG. 9C show the experimental results of the kinetic test and peak statistics by the method being the same as that in step 4 in section II of Example 1, respectively. The left panel and the right panel of FIG. 9D show the experimental results of the kinetic test and peak statistics of the graphene-based single molecule device containing the microcavity with 30 μL of DTT buffer containing 100 nM template strand G, 5 μL of dATP solution, 5 μL of dGTP solution and 5 μL of dTTP solution, respectively. The left panel and the right panel of FIG. 9E show the experimental results of the kinetic test and peak statistics of the graphene-based single molecule device containing the microcavity with 30 μL of DTT buffer containing 100 nM template strand G and 5 μL of dCTP solution, respectively.
Figure 9:
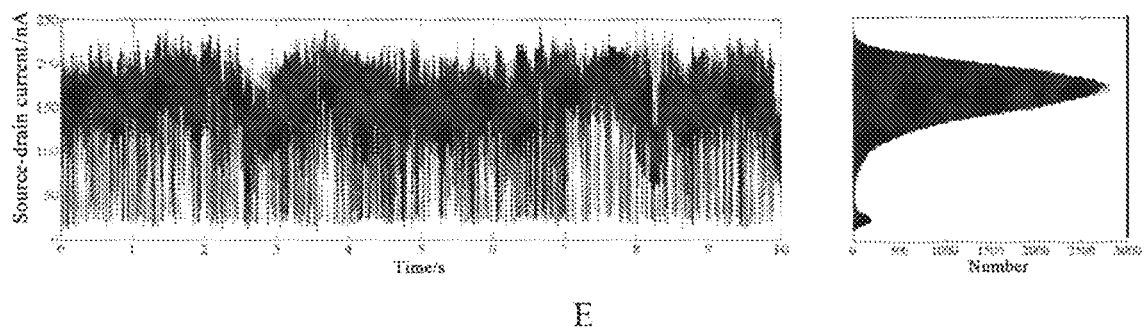
Figure 10:
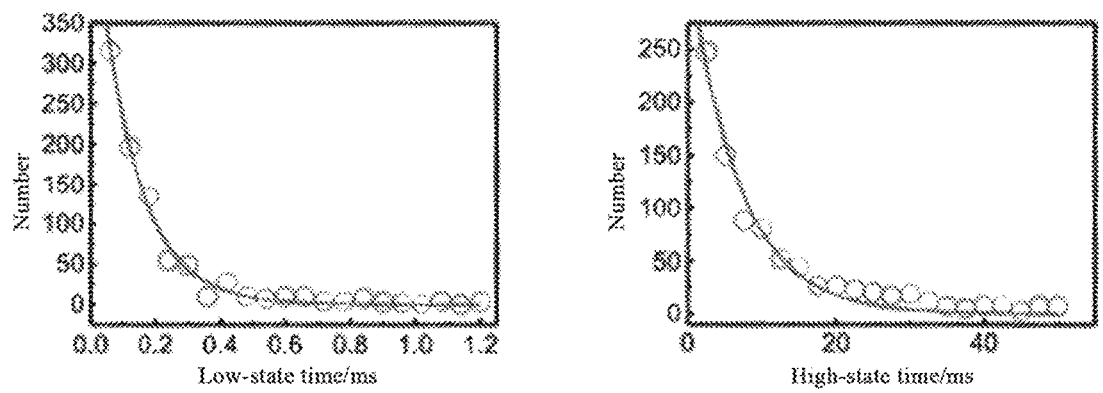
FIG. 10 is statistical analysis results of high-state and low-state time obtained from DNA sequencing of template strand G using a graphene-based single molecule device modified by DNA polymerase.

IV. DNA Sequencing of Template Stand G Using a Graphene-Based Single Molecule Device Modified by DNA Polymerase 1. The method is the same as that in step II-1.
2. The method is the same as that in step II-2. The experimental results of the kinetic test are shown in the left panel of FIG. 9A. The experimental results of peak statistics are shown in the right panel of FIG. 9A, indicating that no oscillation signal of DNA synthesis was observed in the absence of sample.
3. The method is the same as that in step II-3. The experimental results of the kinetic test are shown in the left panel of FIG. 9B. The experimental results of peak statistics are shown in the right panel of FIG. 9B, indicating that no oscillation signal of DNA synthesis was observed in the presence of buffer alone and in the absence of sample.
4. The method is the same as that in step II-4, except that the template strand C is substituted with a template strand G. The experimental results of the kinetic test are shown in the left panel of FIG. 9C. The experimental results of peak statistics are shown in the right panel of FIG. 9C, indicating that no oscillation signal of DNA synthesis was observed in the presence of template strand and buffer and in the absence of sample.
5. After completion of step 1, the microcavity in the graphene-based single molecule device containing the same was added with 30 μL of DTT buffer containing 100 nM template strand G, 5 μL of dATP solution (at a concentration of 5 μM), 5 μL of dGTP solution (at a concentration of 5 M) and 5 μL of dTTP solution (at a concentration of 5 M), and sampled for 10 minutes for a kinetic test (i.e., testing changes of source-drain current over time). The experimental results are shown in the left panel of FIG. 9D. The preliminary peak statistics were then performed using MatLab software. The experimental results are shown in the right panel of FIG. 9D, indicating that no oscillation signal of DNA synthesis was observed in the case that template strand, nucleic acid molecules, and buffer are present but the bases are not matched.
6. After completion of step 1, the microcavity in the graphene-based single molecule device containing the same was added with 30 μL of DTT buffer containing 100 nM template strand G and 5 μL of dCTP solution (at a concentration of 5 μM), and sampled for 10 minutes to test the change of source-drain current over time during DNA synthesis performed by DNA polymerase, i.e., the kinetic data during DNA polymerization performed by DNA polymerase. The experimental results are shown in the left panel of FIG. 9E. The preliminary peak statistics were then performed using MatLab software. The experimental results are shown in the right panel of FIG. 9E, indicating that the oscillation signal of DNA synthesis was observed in the case that template strand, nucleic acid molecules, and buffer are present and the bases are matched. The results show that the kinetic data in step 6 are essentially different from those in other control experiments apparently, that is, when template strand G and the deoxynucleotide matching with it are present in the system, the kinetic data of the system can be different from those of other four groups of control experiments.
7. According to the method of step II-7, a high-state time corresponding to the high-state current ($\tau_{hi}$) and a low-state time corresponding to the low-state current ($\tau_{low}$) were statistically analyzed. The experimental results are shown in FIG. 10 (the left panel shows the low-state time, and the right panel shows the high-state time). The rate of DNA synthesis in this system was calculated to be 143.99 dCTP nucleotides per second (see Table 1) according to an average low-state time and an average high-state time, which is substantially consistent with the synthesis rate described in the previous document (Tivoli J. Olsen, Yongki Choi, Patrick C. Sims, O. Tolga Gul, Brad L. Corso, Chengjun Dong, William A. Brown, Philip G. Collins and Gregory A. Weiss, Electronic Measurements of Single-Molecule Processing by DNA Polymerase I (Klenow Fragment), Journal of the American Chemical Society 2013, 135, 7855-7860).

Figure 11:
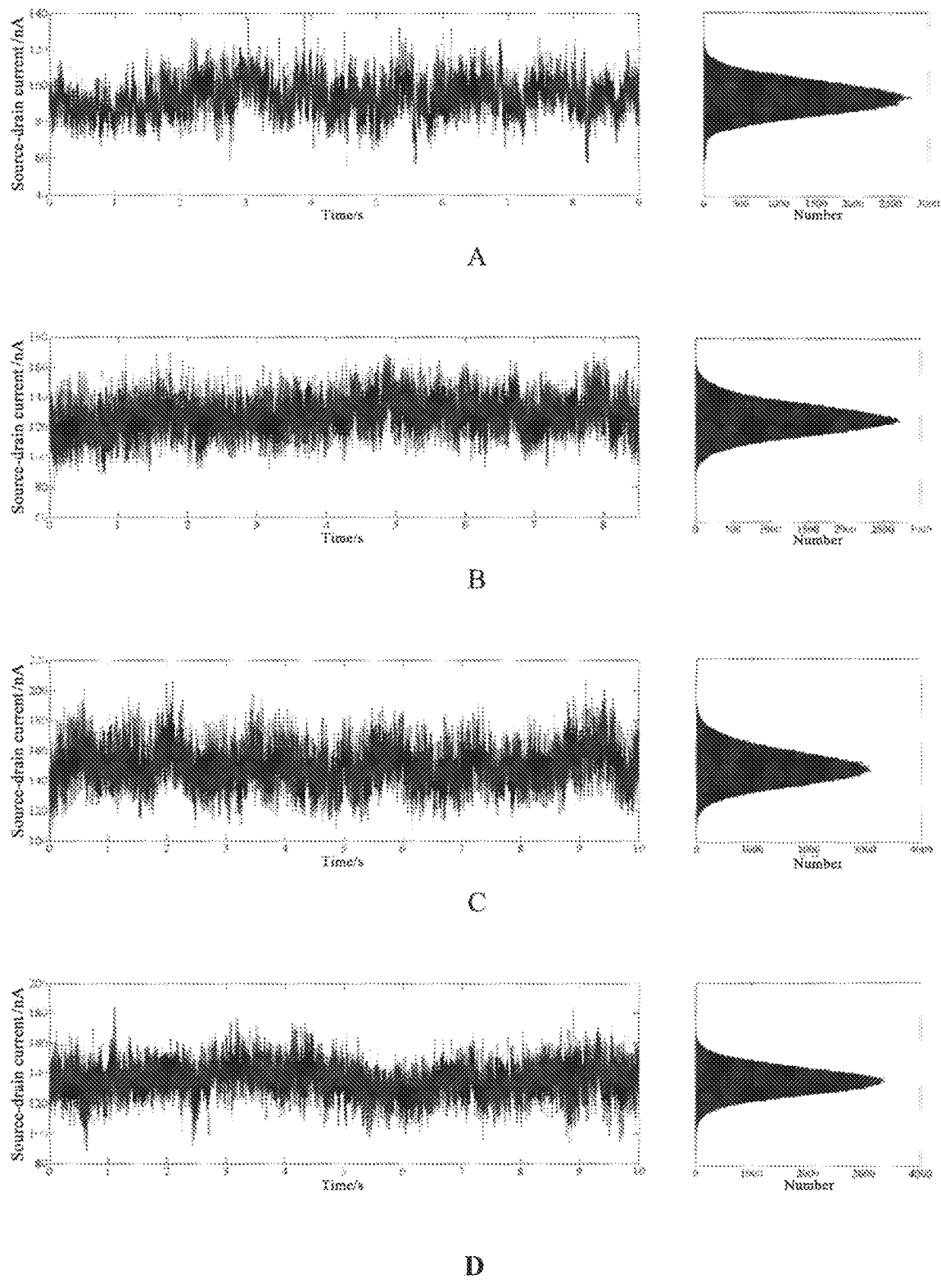
FIG. 11 is kinetic data and peak statistical results of DNA sequencing obtained from template strand T using a graphene-based single molecule device modified by DNA polymerase. The left panel and the right panel of FIG. 11A show the experimental results of the kinetic test and peak statistics by the method being the same as that in step 2 in section II of Example 1, respectively. The left panel and the right panel of FIG. 11B show the experimental results of the kinetic test and peak statistics by the method being the same as that in step 3 in section II of Example 1, respectively. The left panel and the right panel of FIG. 11C show the experimental results of the kinetic test and peak statistics by the method being the same as that in step 4 in section II of Example 1, respectively. The left panel and the right panel of FIG. 11D show the experimental results of the kinetic test and peak statistics of the graphene-based single molecule device containing the microcavity with 100 nM template strand T in 30 μL of DTT buffer, 5 μL of dCTP solution, 5 μL of dGTP solution and 5 μL of dTTP solution, respectively. The left panel and the right panel of FIG. 11E show the experimental results of the kinetic test and peak statistics of the graphene-based single molecule device containing the microcavity with 100 nM template strand T in 30 μL of DTT buffer and 5 μL of dATP solution, respectively.
Figure 11:
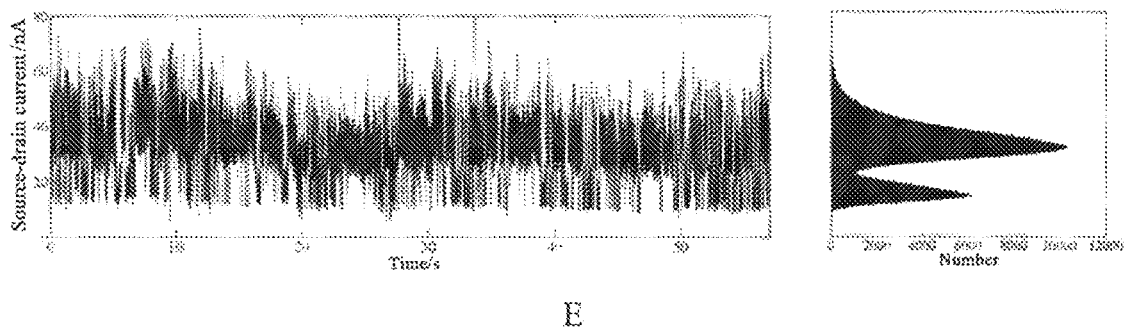

V. DNA Sequencing of Template Stand T Using a Graphene-Based Single Molecule Device Modified by DNA Polymerase 1. The method is the same as that in step II-1.
2. The method is the same as that in step II-2. The experimental results of the kinetic test are shown in the left panel of FIG. 11A. The experimental results of peak statistics are shown in the right panel of FIG. 11A, indicating that no oscillation signal of DNA synthesis was observed in the absence of sample.
3. The method is the same as that in step II-3. The experimental results of the kinetic test are shown in the left panel of FIG. 11B. The experimental results of peak statistics are shown in the right panel of FIG. 11B, indicating that no oscillation signal of DNA synthesis was observed in the presence of buffer alone and in the absence of sample.
4. The method is the same as that in step II-4, except that the template strand C is substituted with a template strand T. The experimental results of the kinetic test are shown in the left panel of FIG. 11C. The experimental results of peak statistics are shown in the right panel of FIG. 11C, indicating that no oscillation signal of DNA synthesis was observed in the presence of template strand and buffer and in the absence of sample.
5. After completion of step 1, the microcavity in the graphene-based single molecule device containing the same was added with 100 nM template strand T in 30 μL of DTT buffer, 5 μL of dCTP solution (at a concentration of 5 M), 5 μL of dGTP solution (at a concentration of 5 μM) and 5 μL of dTTP solution (at a concentration of 5 M), and sampled for 10 minutes for a kinetic test (i.e., testing changes of source-drain current over time). The experimental results are shown in the left panel of FIG. 11D. The preliminary peak statistics were then performed using MatLab software. The experimental results are shown in the right panel of FIG. 11D, indicating that no oscillation signal of DNA synthesis was observed in the case that template strand, nucleic acid molecules, and buffer are present but the bases are not matched.

6. After completion of step 1, the microcavity in the graphene-based single molecule device containing the same was added with 100 nM template strand T in 30 μL of DTT buffer and 5 μL of dATP solution (at a concentration of 5 μM), and sampled for 10 minutes to test changes of source-drain current over time during DNA synthesis performed by DNA polymerase, i.e., the kinetic data during DNA polymerization performed by DNA polymerase. The experimental results are shown in the left panel of FIG. 11E. The preliminary peak statistics were then performed using MatLab software. The experimental results are shown in the right panel of FIG. 11E, indicating that the oscillation signal of DNA synthesis was observed in the case that template strand, nucleic acid molecules, and buffer are present and the bases are matched.

Figure 12:
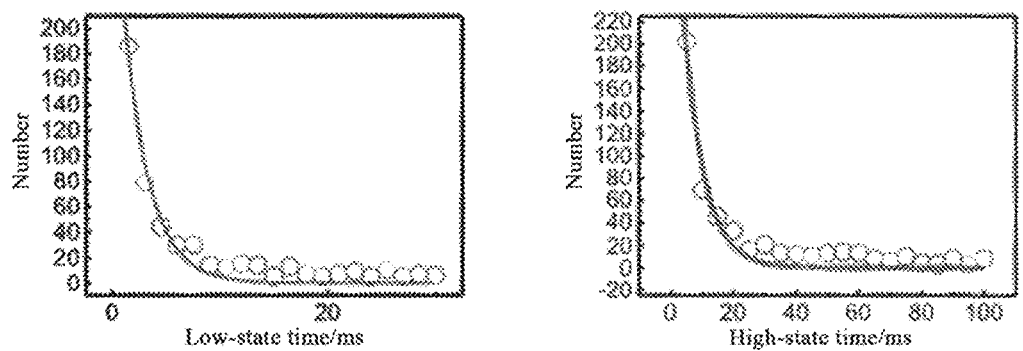
FIG. 12 is statistical analysis results of high-state and low-state time obtained from DNA sequencing of template strand T using a graphene-based single molecule device modified by DNA polymerase.

The results show that the kinetic data in step 6 are essentially different from those in other control experiments apparently, that is, when template strand T and the deoxynucleotide matching with it are present in the system, the kinetic data of the system can be different from those of other four groups of control experiments. 7. According to the method of step II-7, a high-state time corresponding to a high-state current (Thi) and a low-state time corresponding to a low-state current (Tlow) were statistically analyzed. The experimental results are shown in FIG. 12 (the left panel shows the low-state time, and the right panel shows the high-state time). The rate of DNA synthesis in this system was calculated to be 232.83 dATP nucleotides per second (see Table 1) according to the average low-state time and the average high-state time, which is substantially consistent with the synthesis rate described in the previous document (Tivoli J. Olsen, Yongki Choi, Patrick C. Sims, O. Tolga Gul, Brad L. Corso, Chengjun Dong, William A. Brown, Philip G. Collins and Gregory A. Weiss, Electronic Measurements of Single-Molecule Processing by DNA Polymerase I (Klenow Fragment), Journal of the American Chemical Society 2013, 135, 7855-7860).

Figure 13:
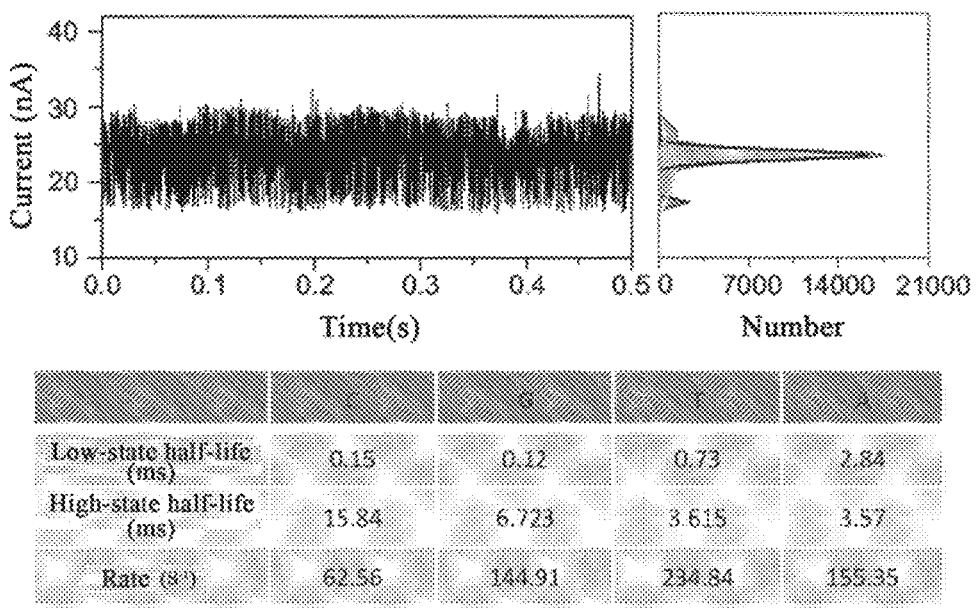
FIG. 13 is statistical analysis results of high-state and low-state time obtained from DNA sequencing of a random strand using a graphene-based single molecule device modified by DNA polymerase.

VI. DNA Sequencing of Random Sequence Using a Graphene-Based Single Molecule Device Modified by DNA Polymerase After completion of step 1, the microcavity in the graphene-based single molecule device containing the same was added with 100 nM random strand (SEQ ID NO. 9) in 30 μL of DTT buffer and 5 μL of solution (containing dATP, dGTP, dCTP, and dTTP at a concentration of 5 μM), and sampled for 10 minutes to test changes of source-drain current over time during DNA synthesis performed by DNA polymerase, i.e., the kinetic data during DNA polymerization performed by DNA polymerase. The experimental results are shown in FIG. 13, showing four different oscillation signals. The preliminary peak statistics were then performed using MatLab software. The experimental results are shown in the table of FIG. 13. From the data in this table and Table 1, the bases corresponding to different currents can be determined, thereby determining DNA sequence according to changes of current. Therefore, the graphene-based single molecule device modified by DNA polymerase can be used to perform DNA sequencing.

Example 2. DNA Sequencing Using a Silicon Nanowire Single Molecule Device Modified by DNA Polymerase I. Preparation of a Silicon Nanowire Single Molecule Device Modified by DNA Polymerase 1. Preparation of a Silicon Nanowire Single Molecule Device The preparation process of a silicon nanowire single molecule device can be referred to the following document: Cao Y, Dong S, Liu S, He L, Gan L, Yu X, Steigerwald M L, Wu X, Liu Z, Guo X. Building high-throughput molecular junctions using indented graphene point contacts. Angew Chem Int Ed Engl. 2012 Dec. 3; 51(49): 12228-32. There is a silicon nanowire electrode having nanogap (hereinafter referred to as a silicon nanowire electrode) on the silicon nanowire single molecule device.

The following steps 2 to 7 were performed according to the methods reported in the document (Gen He, Jie Li, Haina Ci, Chuanmin Qi*, and Xuefeng Guo*, Direct measurement of single-molecule DNA hybridization dynamics with single-base resolution, Angew. Chem. Int. Ed. 2016, 55, 9036).

2. Etching

After completion of step 1, the silicon nanowire single molecule device was mixed with HF solution to obtain an etched silicon nanowire single molecule device. The schematic diagram of partial structure of the etched silicon nanowire single molecule device is shown in FIG. 14 (1).

3. Construction of an Electrical Circuit

Figure 14:
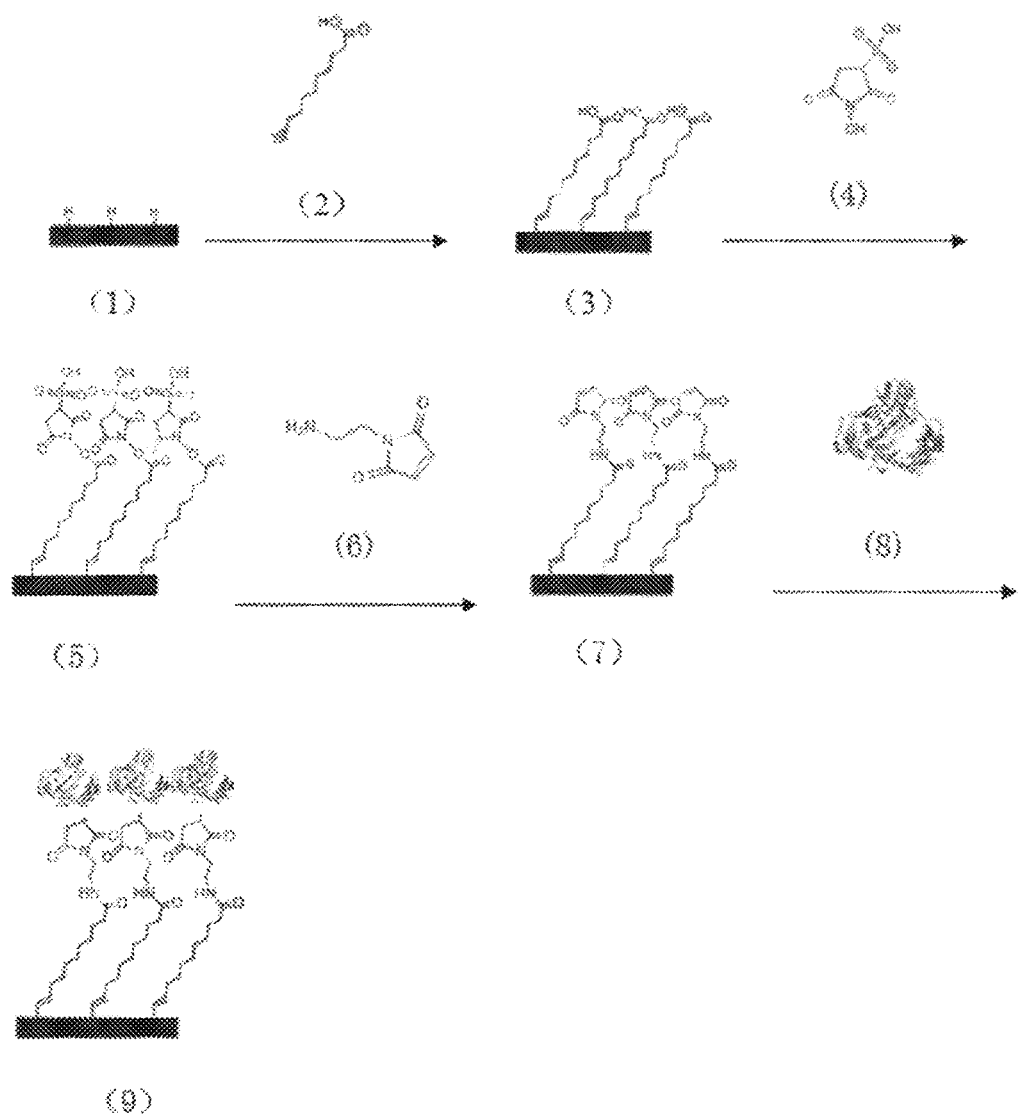
FIG. 14 shows the preparation of a silicon nanowire single molecule device modified by DNA polymerase.

After completion of step 2, the etched silicon nanowire single molecule device was mixed with 10-undecynoic acid (see FIG. 14 (2)) to obtain an electrical circuit. The schematic diagram of partial structure of the electrical circuit is shown in FIG. 14 (3)

4. Sulfo-NHS Activation

After completion of step 3, the electrical circuit was mixed with salt of sodium N-hydroxysulfosuccinimide (Sulfo-NHS, see FIG. 14 (4)) to obtain a Sulfo-NHS activated electrical circuit. The partial structural formula of the Sulfo-NHS activated electrical circuit is shown in FIG. 14 (5).

5. Acquisition of a Treated Silicon Nanowire Single Molecule Device

After completion of step 4, the Sulfo-NHS activated electrical circuit was mixed with N-(2-aminoethyl)maleimide hydrochloride (see FIG. 14 (6)) to obtain a treated silicon nanowire single molecule device. The partial structural formula of the treated silicon nanowire single molecule device is shown in FIG. 14 (7).

6. Reconstruction of *E. coli* DNA Polymerase I

The method is the same as that in step I-6 of Example 1.

7. Preparation of a Silicon Nanowire Single Molecule Device Modified by DNA Polymerase After completion of step 6, the treated silicon nanowire single molecule device was mixed with reconstructed DNA polymerase I (see FIG. 14 (8)) in an excess amount to obtain a silicon nanowire single molecule device modified by DNA polymerase (see the right panel of FIG. 3). The schematic diagram of partial structure of the silicon nanowire single molecule device modified by DNA polymerase is shown in FIG. 14 (9).

The prepared silicon nanowire single molecule device modified by DNA polymerase was placed on a low-resolution probe station to observe conductivity. The silicon nanowire single molecule device modified by DNA polymerase having conductivity was used for the following experiments.

II. DNA Sequencing of Template Stand C Using a Silicon Nanowire Single Molecule Device Modified by DNA Polymerase According to the method in step II of Example 1, the graphene-based single molecule device modified by DNA polymerase was replaced with a silicon nanowire single molecule device modified by DNA polymerase, without changing other steps. The obtained DNA synthesis rate in this system is 65.30 dGTP nucleotides per second, which is not significantly different from the results of DNA sequencing of template strand C using the graphene-based single molecule device modified by DNA polymerase.

III. DNA Sequencing of Template Stand a Using a Silicon Nanowire Single Molecule Device Modified by DNA Polymerase According to the method in step III of Example 1, the graphene-based single molecule device modified by DNA polymerase was replaced with a silicon nanowire single molecule device modified by DNA polymerase, without changing other steps. The obtained DNA synthesis rate in this system is 117.27 dTTP nucleotides per second, which is not significantly different from the results of DNA sequencing of template strand A using the graphene-based single molecule device modified by DNA polymerase.

IV. DNA Sequencing of Template Stand G Using a Silicon Nanowire Single Molecule Device Modified by DNA Polymerase According to the method in step IV of Example 1, the graphene-based single molecule device modified by DNA polymerase was replaced with a silicon nanowire single molecule device modified by DNA polymerase, without changing other steps. The obtained DNA synthesis rate in this system is 154.51 dCTP nucleotides per second, which is not significantly different from the results of DNA sequencing of template strand G using the graphene-based single molecule device modified by DNA polymerase.

V. DNA Sequencing of Template Stand T Using a Silicon Nanowire Single Molecule Device Modified by DNA Polymerase According to the method in step V of Example 1, the graphene-based single molecule device modified by DNA polymerase was replaced with a silicon nanowire single molecule device modified by DNA polymerase, without changing other steps. The measured oscillation signals of DNA synthesis are consistent with that measured with the graphene-based single molecule device modified by DNA polymerase. The obtained DNA synthesis rate in this system is 234.60 dATP nucleotides per second, which is not significantly different from the results of DNA sequencing of template strand T using the graphene-based single molecule device modified by DNA polymerase.

Therefore, the silicon nanowire single molecule device modified by DNA polymerase can be used to perform DNA sequencing.

The invention claimed is:

1. A single molecule device modified by DNA polymerase comprising a DNA polymerase and a single molecule device, wherein the single molecule device is a two-dimensional nanomaterial single molecule device or an one-dimensional nanomaterial single molecule device, and wherein the single molecule device is modified by DNA polymerase and comprises graphene or silicon nanowires as an electrode for responding to a conformation change of the DNA polymerase linking to the electrode; wherein the DNA polymerase has a linkage site linking to the single molecule device, and the linkage site is an amino acid residue located in a conformation changing region of the DNA polymerase;
  wherein the DNA polymerase is a protein having an amino acid sequence consisting of SEQ ID NO. 3, or a functional mutant of the protein having an amino acid sequence consisting of SEQ ID NO. 3;
  wherein the DNA polymerase is linked to the single molecule device via only the linkage site; and
  wherein cysteine residue at position 790 from N terminus of SEQ ID NO. 3 is the amino acid residue located in the conformation changing region of the DNA polymerase and is the linkage site.

2. The single molecule device modified by DNA polymerase according to claim 1, wherein the DNA polymerase linking to the single molecule device is contained in a microcavity of the single molecule device.

3. The single molecule device modified by DNA polymerase according to claim 2, wherein the microcavity is made of polydimethylsiloxane.

4. A kit for DNA sequencing comprising
  the single molecule device modified by DNA polymerase of claim 1.

5. The kit according to claim 4, wherein the DNA polymerase and the single molecule device are present in separate compartments, and are linked to each other; or
  the DNA polymerase is linked to the single molecule device.

6. The kit according to claim 4, further comprising a sequencing primer, dNTPs and/or an instruction for using the kit.

* * * * *